(12) United States Patent
Buckland et al.

(10) Patent No.: US 8,864,309 B2
(45) Date of Patent: Oct. 21, 2014

(54) OPTICAL IMAGING SYSTEMS HAVING INPUT BEAM SHAPE CONTROL AND PATH LENGTH CONTROL

(71) Applicant: Bioptigen, Inc., Morrisville, NC (US)

(72) Inventors: Eric L. Buckland, Hickory, NC (US); Andrew Murnan, Saratoga Springs, NY (US); Christopher Saxer, Chapel Hill, NC (US); Robert H. Hart, Cary, NC (US); Nestor O. Farmiga, Rochester, NY (US)

(73) Assignee: Bioptigen, Inc., Morrisville, NC (US)

( * ) Notice: Subject to any disclaimer, the term of this patent is extended or adjusted under 35 U.S.C. 154(b) by 2 days.

(21) Appl. No.: 13/705,867

(22) Filed: Dec. 5, 2012

(65) Prior Publication Data
US 2013/0141695 A1    Jun. 6, 2013

Related U.S. Application Data

(60) Provisional application No. 61/566,856, filed on Dec. 5, 2011, provisional application No. 61/620,645, filed on Apr. 5, 2012.

(51) Int. Cl.
| | |
|---|---|
| *A61B 3/14* | (2006.01) |
| *G02B 13/22* | (2006.01) |
| *A61B 5/00* | (2006.01) |
| *G02B 26/10* | (2006.01) |
| *A61B 3/10* | (2006.01) |

(52) U.S. Cl.
CPC ............ *A61B 3/102* (2013.01); *G02B 13/22* (2013.01); *A61B 5/0066* (2013.01); *G02B 26/101* (2013.01)

USPC ........................................................ 351/206

(58) Field of Classification Search
USPC .......... 351/206, 221, 246; 356/497, 512, 489, 356/495, 511
See application file for complete search history.

(56) References Cited

U.S. PATENT DOCUMENTS

| | | |
|---|---|---|
| 4,561,080 A | 12/1985 | Yamazaki |
| 5,055,663 A | 10/1991 | Morimoto et al. |
| 5,103,439 A | 4/1992 | Bierhoff et al. |
| 5,168,386 A | 12/1992 | Galbraith |
| 5,491,524 A | 2/1996 | Hellmuth et al. |

(Continued)

FOREIGN PATENT DOCUMENTS

| | | |
|---|---|---|
| EP | 0 697 611 A1 | 2/1996 |
| EP | 0 697 611 A2 | 2/1996 |
| EP | 1 659 438 B1 | 11/2001 |

OTHER PUBLICATIONS

Qi et al., "Dynamic focus control in high-speed optical coherence tomography based on a microelectromechanical mirror," Optics Communications, 232 (2004) pp. 123-128.

(Continued)

*Primary Examiner* — Hung Dang
(74) *Attorney, Agent, or Firm* — Myers Bigel Sibley & Sajovec

(57) ABSTRACT

Scanning optical beam imaging systems for imaging a surface with convex curvature are provided. The systems include a sphero-telecentric objective, wherein a scanning radius of curvature of the sphero-telecentric objective is greater than an apical radius of curvature of the surface and less than or equal to four times an apical radius of curvature of the surface.

9 Claims, 35 Drawing Sheets a: FIBER INPUT
b: COLLIMATOR
c: INPUT BEAM SHAPE CONTROL
d: MIRROR AXIS 1
e: TELECENTRIC RELAY HALF 1
f: TELECENTRIC RELAY HALF 2
g: MIRROR AXIS 2
h: TELECENTRIC RELAY HALF 3
i: RELAY BEAM EXPANDER
j: IMAGING LENS
k: SUBJECT

(56) References Cited

U.S. PATENT DOCUMENTS

| | | | |
|---|---|---|---|
| 5,493,109 | A | 2/1996 | Wei et al. |
| 5,795,295 | A | 8/1998 | Hellmuth et al. |
| 5,889,750 | A | 3/1999 | Summers et al. |
| 6,004,314 | A | 12/1999 | Wei et al. |
| 6,419,360 | B1 * | 7/2002 | Hauger et al. ............... 351/206 |
| 6,426,840 | B1 | 7/2002 | Partanen et al. |
| 6,763,259 | B1 | 7/2004 | Hauger et al. |
| 7,699,468 | B2 | 4/2010 | Gaida |
| 7,719,692 | B2 | 5/2010 | Izatt et al. |
| 7,742,174 | B2 | 6/2010 | Izatt et al. |
| 7,791,794 | B2 | 9/2010 | Reimer et al. |
| 7,839,494 | B2 | 11/2010 | Reimer et al. |
| 7,889,423 | B2 | 2/2011 | Reimer et al. |
| 7,901,080 | B2 | 3/2011 | Hauger et al. |
| 8,023,120 | B2 | 9/2011 | Reimer et al. |
| 8,049,873 | B2 | 11/2011 | Hauger et al. |
| 8,189,192 | B2 | 5/2012 | Huening et al. |
| 8,310,674 | B2 | 11/2012 | Huening et al. |
| 8,348,427 | B2 | 1/2013 | Buckland et al. |
| 8,401,257 | B2 | 3/2013 | Izatt et al. |
| 8,425,037 | B2 | 4/2013 | Uhlhorn et al. |
| 8,625,104 | B2 | 1/2014 | Izatt et al. |
| 8,693,745 | B2 | 4/2014 | Izatt et al. |
| 2003/0218755 | A1 | 11/2003 | Wei et al. |
| 2007/0030446 | A1 | 2/2007 | Su et al. |
| 2007/0291277 | A1 | 12/2007 | Everett et al. |
| 2010/0309478 | A1 | 12/2010 | Reimer et al. |
| 2011/0028948 | A1 | 2/2011 | Raksi et al. |
| 2012/0242988 | A1 | 9/2012 | Saxer et al. |
| 2012/0262720 | A1 | 10/2012 | Brown et al. |
| 2013/0141695 | A1 | 6/2013 | Buckland et al. |
| 2013/0265545 | A1 | 10/2013 | Buckland et al. |

OTHER PUBLICATIONS

Geerling et al., "Intraoperative 2-Dimensional Optical Coherence Tomography as a New Tool for Anterior Segment Surgery," Arch Ophthalmol, vol. 123, Feb. 2005, pp. 253-257.

Dal Maschio et al. "Three-dimensional in vivo scanning microscopy with inertia-free focus control," Optics Letters, vol. 36, No. 17, Sep. 1, 2011, pp. 3503-3505.

Notification of Transmittal of the International Search Report and the Written Opinion of the International Searching Authority, or the Declaration, PCT/US2013/034544, Jul. 3, 2013.

Notification of Transmittal of the International Search Report and the Written Opinion of the International Searching Authority, of the Declaration, PCT/US2012/067951, Mar. 5, 2013.

* cited by examiner

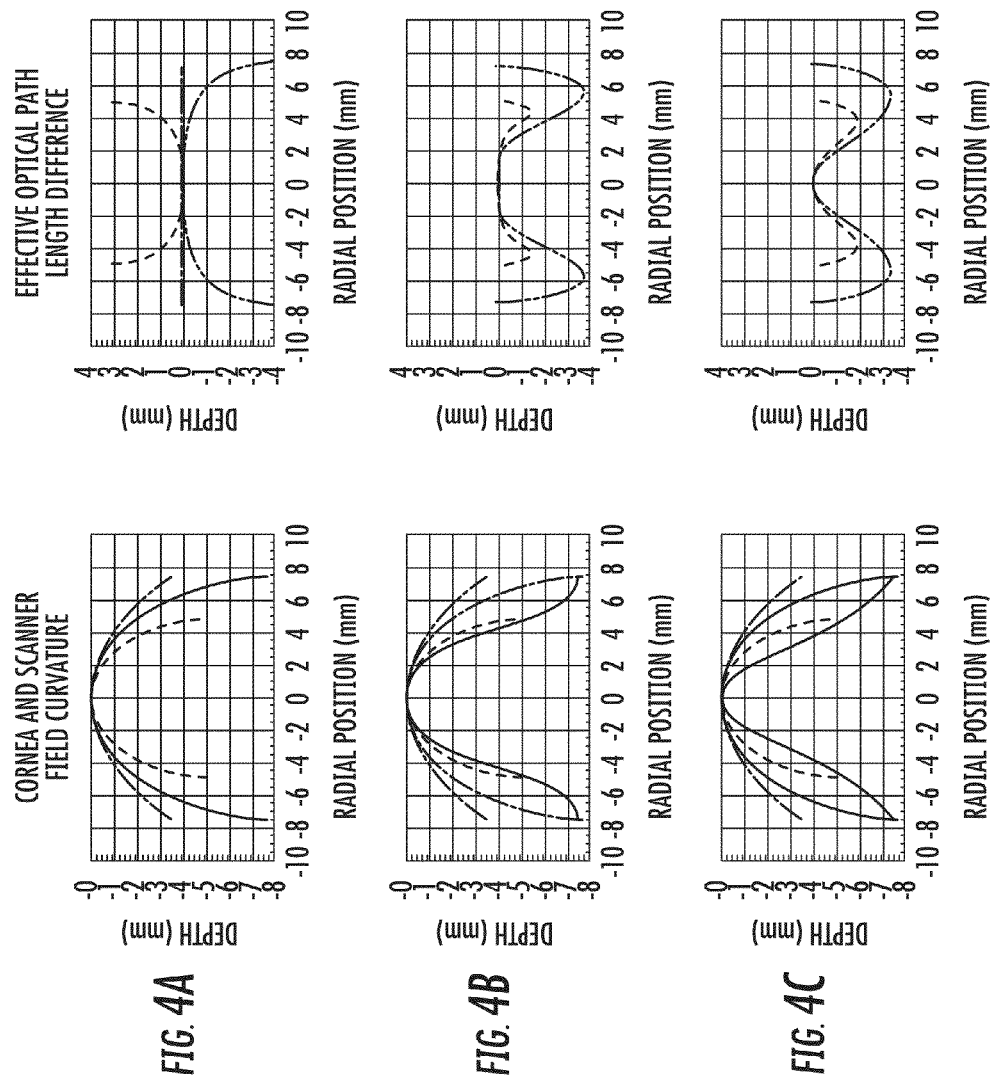

INPUT SINGLE MODE FIBER FOLLOWED BY MOVABLE POSITIVE LENS

INPUT LASER SOURCE FOLLOWED BY MOVEABLE POSITIVE LENS, MOVABLE NEGATIVE LENS, AND OPTIONAL FIXED POSITIVE LENS

INPUT SINGLE MODE FIBER FOLLOWED BY FIXED POSITIVE LENS FOLLOWED BY MOVABLE POSITIVE LENS

A: INPUT SINGLE MODE FIBER FOLLOWED BY COLLIMATING LENS, FOLLOWED BY POSITIVE LENS, FOLLOWED BY MOVABLE NEGATIVE LENS, FOLLOWED BY MOVABLE POSITIVE LENS

A': INPUT SINGLE MODE FIBER FOLLOWED BY A FIRST LENS SYSTEM WITH INPUT NA AND EXIT NA AND INPUT FOCAL LENGTH AND OUTPUT FOCAL LENGTH, FOLLOWED BY MOVABLE NEGATIVE LENS, FOLLOWED BY MOVABLE POSITIVE LENS

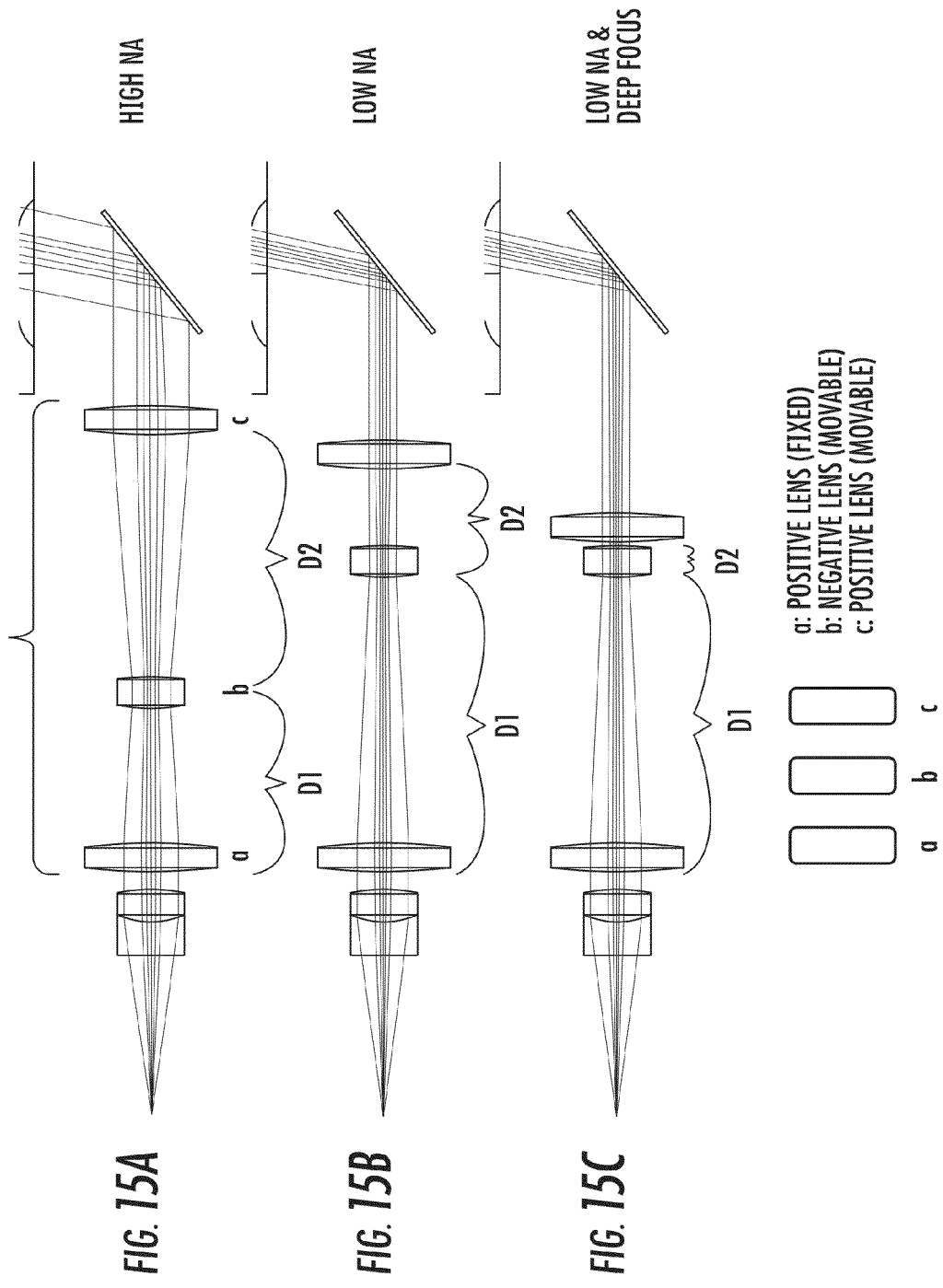

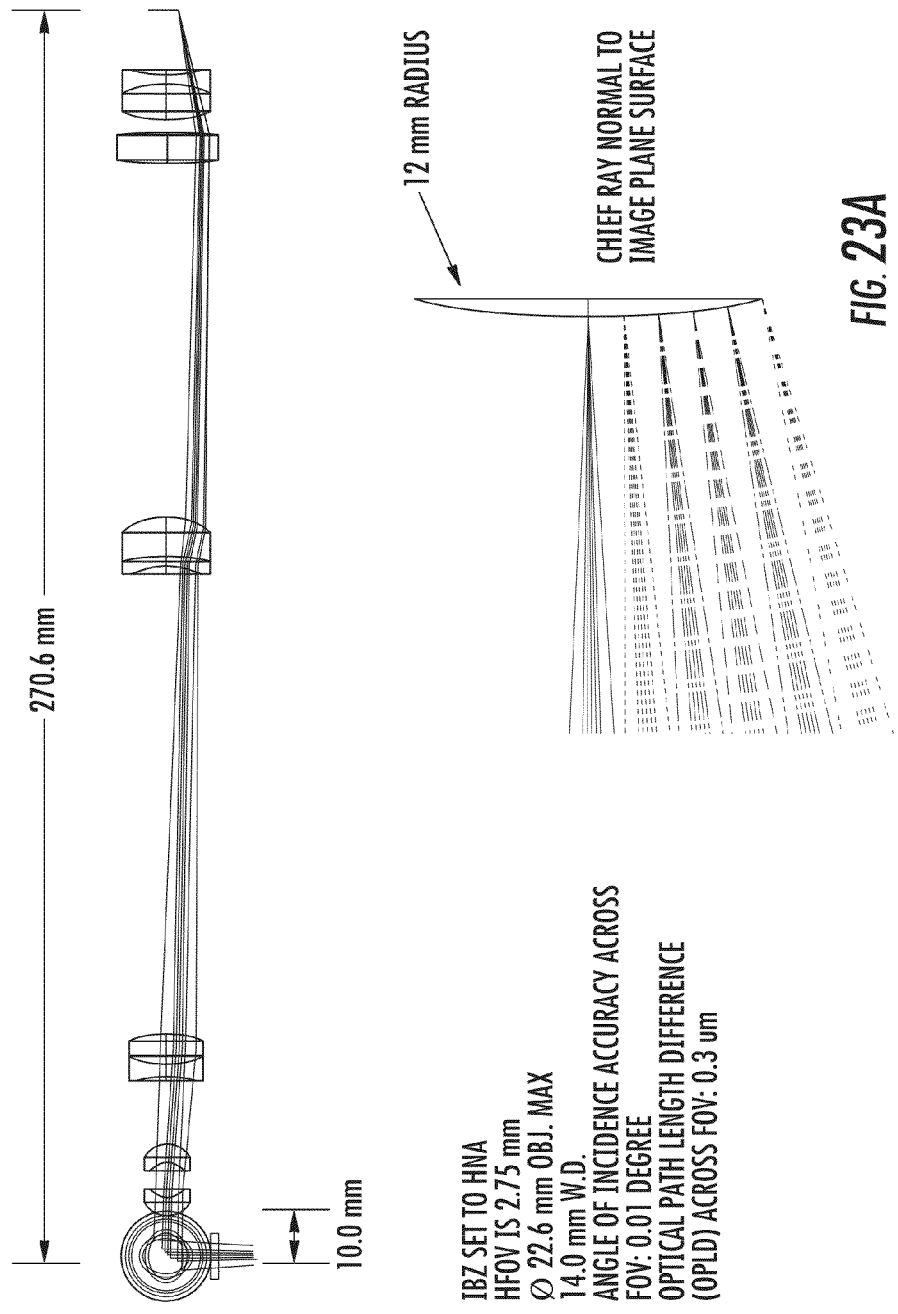

FIG. 30A

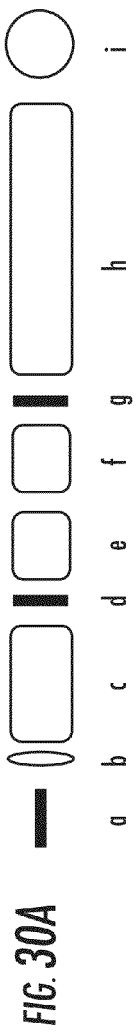

FIG. 30B

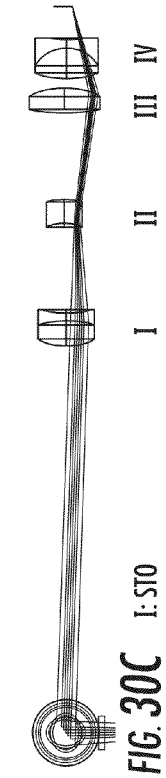

| IBZ | POWER [D] |
|---|---|
| LENS a | 25.6 |
| LENS b | -87.7 |
| LENS c | 25.6 |

FIG. 30C

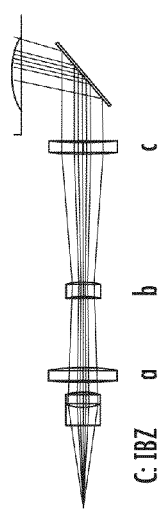

I: STO

| OBJECTIVE | POWER [D] | LENS TYPE | LENS SHAPE | SPACING TO PREVIOUS LENS [mm] | COMMENTS |
|---|---|---|---|---|---|
| LENS I | 34 | SINGLET | MENISCUS | 24 | SPACING FROM 2ND GALVO |
| LENS II | -65 | DOUBLET | MENISCUS | 9 | |
| LENS III | 20 | SINGLET | BICONVEX | 84 | MILD ASPHERE ON SURFACE NEAREST TO GALVO |
| LENS IV | 12 | DOUBLET | MENISCUS | 3 | 14 mm W.D. TO CORNEA |

MODE 1 (IMAGING MODE)

| FOCUS POSITION | LENS a - LENS b SPACING [mm] | LENS a - LENS b SPACING [mm] | PATHLENGTH [mm] | FOV [mm] |
|---|---|---|---|---|
| CORNEA | 10.4 | 18.6 | 545 | 5.4 |
| ANTERIOR MIDPOINT | 10.4 | 17.8 | 547.5 | 4.8 |
| PUPIL PLANE | 10.4 | 16.6 | 549.9 | 3.8 |
| POSTERIOR LENS SURFACE | 10.4 | 8.6 | 555.2 | 1.8 |
| RETINA | 10.4 | 23.8 | 577.3 | 7.6 |

MODE 3 (COMBINED IMAGING / BIOMETRY MODE)

| FOCUS POSITION | LENS a - LENS b SPACING [mm] | LENS a - LENS b SPACING [mm] | PATHLENGTH [mm] | FOV [mm] |
|---|---|---|---|---|
| CORNEA | 45.4 | 33.3 | 545 | 5.4 |
| ANTERIOR MIDPOINT | 44.2 | 33 | 547.5 | 4.8 |
| PUPIL PLANE | 42.8 | 32.6 | 549.9 | 3.8 |
| POSTERIOR LENS SURFACE | 37.2 | 31.1 | 555.2 | 1.8 |
| POSTERIOR MIDPOINT | 14.3 | 24.9 | 566.3 | 3 |
| RETINA | 10.4 | 23.8 | 577.3 | 7.6 |

OPTICAL IMAGING SYSTEMS HAVING INPUT BEAM SHAPE CONTROL AND PATH LENGTH CONTROL

CLAIM OF PRIORITY

The present application claims priority from U.S. Provisional Application No. 61/566,856, filed Dec. 5, 2011, and U.S. Provisional Application No. 61/620,645, filed Apr. 5, 2012, the disclosure of which is hereby incorporated herein by reference as if set forth in its entirety.

STATEMENT OF GOVERNMENT SUPPORT

This invention was funded in-part with government support under Grant Application ID 1R43EY022835-01 entitled Aspheric SDOCT Imaging System for Dry Eye and Cornea Diagnostics by the National Institutes of Health, National Eye Institute. The United States Government has certain rights in this invention.

FIELD

The present inventive concept relates to imaging and, more particularly, optical coherence tomography (OCT) systems having constant optical path lengths.

BACKGROUND

Dry eye disease is an affliction that impacts as many as 20 percent of the U.S. population over age 50 and may be even more prevalent around the world. Dry eye disease can impact women more than men, and can have a dramatic and negative impact on quality of life and economic productivity. The etiology of dry eye is complex, involving the autoimmune system, and both the exocrine and endocrine systems. Currently, treatment is primary palliative, involving warm compresses and eye drops. RESTASIS provided by Allergan, Inc. seeks to reduce inflammation to promote tear flow. TearScience recently released LipiFlow to attempt to thermally improve meibomian gland function.

Corneal dystrophies include disease and injury of the epithelium, stroma and endothelium. 2.5 million Americans suffer from eye injury each year. There are at least 80,000 corneal transplants and grafts annually. Keratoconus affects 1 in 2000. 35 million Americans wear contact lenses and approximately 3 million Americans undergo some sort of refractive surgery each year. The contact lens industry is 3 billion dollar retail industry, and investment in surgical procedures and devices for management of eye disease and for refractive correction continues to be strong.

Dry eye disease is diagnosed primarily using a patient questionnaire, with support of slit lamp, transdermal illumination, staining, and tear film interferometry. Placido disk cornea topography remains the primary instrument for assessing cornea shape. Each of these visualization techniques is limited in their ability to assess functional causes of dry eye or fine ultrastructure associated with dry eye, tear film, or cornea abnormalities. Additional diagnostic and research techniques are warranted.

The high resolution of spectral domain optical coherence tomography (SDOCT) is beginning to generate interest in cornea imaging. However, like all SDOCT systems that image the anterior with telecentric optics, the signal typically falls off away from cornea center, constraining the field of view. Additionally, away from cornea center the scanning optical coherence tomography beam impinges the cornea at an increasingly oblique angle. The beam then refracts into the cornea. The image on the screen follows the scanning ray; a correct view of the cornea requires a well-understood "dewarping" step.

The issues with respect to SDCOT discussed above are illustrated in, for example, FIGS. 1A-1C. These figures present a selection of inner eye lid images obtained using Spectral Domain Ophthalmic Imaging System provided by Bioptigen, Envisu™ R2300 Spectral Domain Ophthalmic Imaging System. The images in FIGS. 1A-1C illuminate the capabilities of SDOCT in imaging inner eye lid fine structure. In particular, FIG. 1A illustrates a series of B-scan on the left, which follow the path of a Meibomian duct (circled) from the surface of the marginal conductiva to the deeper layers. The image on the right in FIG. 1A is a volume intensity projection through the entire stack of B-scans in a 5 mm×5 mm volumetric image if the marginal conjunctiva area. Referring now to FIG. 1B, the electron micrographs on the right illustrate the distribution of Meibomian glands around the ducts in the tarsal and marginal portion of the conjunctiva. The B-scans on the left appear to illustrate the ducts and surrounding glands in the tarsal conjunctiva of a normal volunteer. The B-Scan on the top also shows what appears to be a global cell. Finally, FIG. 1C illustrates an anatomical drawing of an eyelid showing Meibomian glad on the left. On the right, FIG. 1C illustrates a cross-section of the eyelid to sclera illustrating tear film and two goblets.

Current clinical retina SDOCT systems are increasingly retrofitted for cornea imaging, but as they have a limited imaging depth appropriate for retina, the depth of view for the cornea is wholly inadequate for limbus-limbus imaging of the cornea. Bioptigen (Envisu™ R4300) has developed a deep imaging SDOCT system. As illustrated in FIG. 2, the Bioptigen system has a 7.5 mm depth of view and may be suitable for direct full range imaging of anterior chamber. Thus, this system provides full range anterior segment SDOCT with 7.5 mm depth of view, a 4.0 μm resolution acquired at 20 frames per second.

As further illustrated in FIGS. 3A-I, the Bioptigen system is capable of full depth imaging, but does not solve problem of "warping" due to refraction at the cornea surface. FIGS. 3A-through 3I illustrate a corneoscleral junction with contact lens; keratoconus; riboflavin over partially epithelium stripped cornea after cross-linking; corneal opacity; opacity post treatment with PTK; FS LASIK flap; Microtome LASIK flap; DSAEK with trapped bubble; DSAEK bubble eliminated, respectively. The subject in the image of FIGS. 3A through 3I is wearing a contact lens; the difficulty of oblique imaging is apparent when one tries to resolve the contact lens fit at the limbus. Another problem is that visualization of the angle is hampered, as the scanned ray travels a greater distance through the sclera to reach the angle than would be necessary on normally directed viewing. Accordingly, improved systems are desired.

SUMMARY

Some embodiments of the present inventive concept provide scanning optical beam imaging systems for imaging a surface with convex curvature. The systems include a sphero-telecentric objective, wherein a scanning radius of curvature of the sphero-telecentric objective is greater than an apical radius of curvature of the surface and less than or equal to four times an apical radius of curvature of the surface.

In further embodiments, the sphero-telecentric objective may include lens elements arranged in four or fewer lens groups.

In still further embodiments, the sphero-telecentric objective may include an aspheric optical element.

In some embodiments, the scanning optical beam imaging system may be an optical coherence tomography imaging system.

In further embodiments, the scanning optical beam imaging system may be an input beam zoom. The input beam zoom may include an input light source; a positive lens group in a first position; a movable negative lens group in a second position; a movable positive lens group in a third position, wherein relative positions of the movable negative lens group in the second position to the positive lens group in the first position, and the moveable positive lens group in the third position to the movable negative lens group in the second position control a numerical aperture and a degree of focus of the imaging system.

In still further embodiments, the scanning optical beam imaging system may include a telecentric scanning input. The telecentric scanning input may include an input light source; an input beam shaping system; a first mirror set to scan along a first direction; a first telecentric relay configured to image the first mirror set to a second mirror set to scan along a second direction orthogonal to the first direction; and an objective that receives the telecentrically scanned input beam to a region of a subject.

Some embodiments of the present inventive concept provide ophthalmic optical coherence tomography imaging systems including a sphero-telecentric imaging objective, wherein a scanning radius of curvature of the sphero-telecentric objective is greater than an apical radius of curvature of a cornea of the eye and less than or equal to four times an apical radius of curvature of the cornea of the eye.

In further embodiments, the sphero-telecentric objective may include lens elements arranged in four or fewer lens groups.

In still further embodiments, the sphero-telecentric objective may include an aspheric optical element.

In some embodiments, the optical coherence tomography imaging system may further include an input beam zoom. The input beam zoom may include an input light source; a positive lens group in a first position; a movable negative lens group in a second position; a movable positive lens group in a third position, wherein relative positions of the movable negative lens group in the second position to the positive lens group in the first position, and the movable positive lens group in the third position to the negative lens group in the second position controls a numerical aperture and a degree of focus of the imaging system.

In further embodiments, the optical coherence tomography imaging system may include a telecentric scanning input. The telecentric scanning input may include an input light source; an input beam shaping system; a first mirror set to scan along a first direction; a first telecentric relay that images the first mirror set to a second mirror set to scan along a second direction orthogonal to the first direction; and an objective that receives the telecentrically scanned input beam to a region of a subject.

BRIEF DESCRIPTION OF THE DRAWINGS

FIGS. 4A through 4C are diagrams illustrating sphero-telecentric optical coherence tomography (OCT) field curvature vs. cornea shape.

FIGS. 15A through 15C are a series of block diagrams illustrating operations of input beam shape control for high numerical aperture, low numerical aperture and low numerical aperture with deep focus, respectively, in accordance with some embodiments of the present inventive concept.

FIGS. 23A and 23B are diagrams illustrating elements of sphero-telecentric systems having a 12 mm radius of curvature in accordance with some embodiments of the present inventive concept.

FIGS. 30A-30C are a series of block diagrams illustrating example settings for various modes in accordance with some embodiments of the present inventive concept.

DETAILED DESCRIPTION

Figure 1:
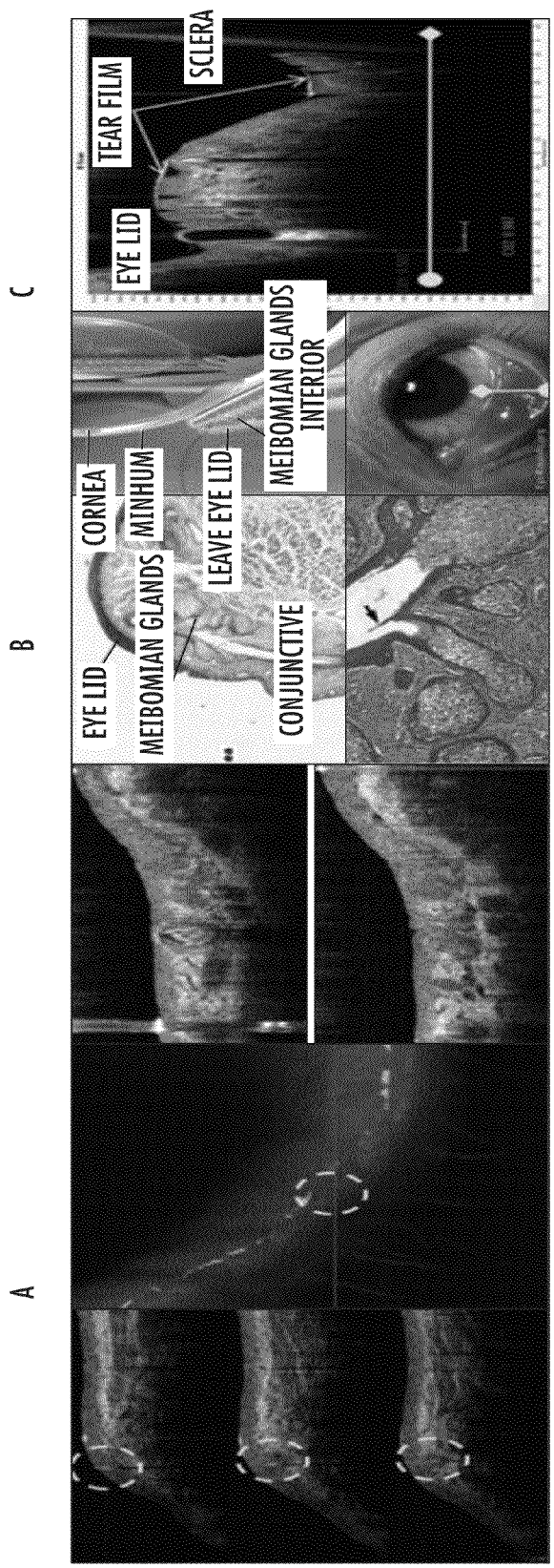
FIGS. 1A-1C are a series of inner eye lid images obtained using Spectral Domain Ophthalmic Imaging System provide by Bioptigen, Envisu™ R2300.
Figure 2:
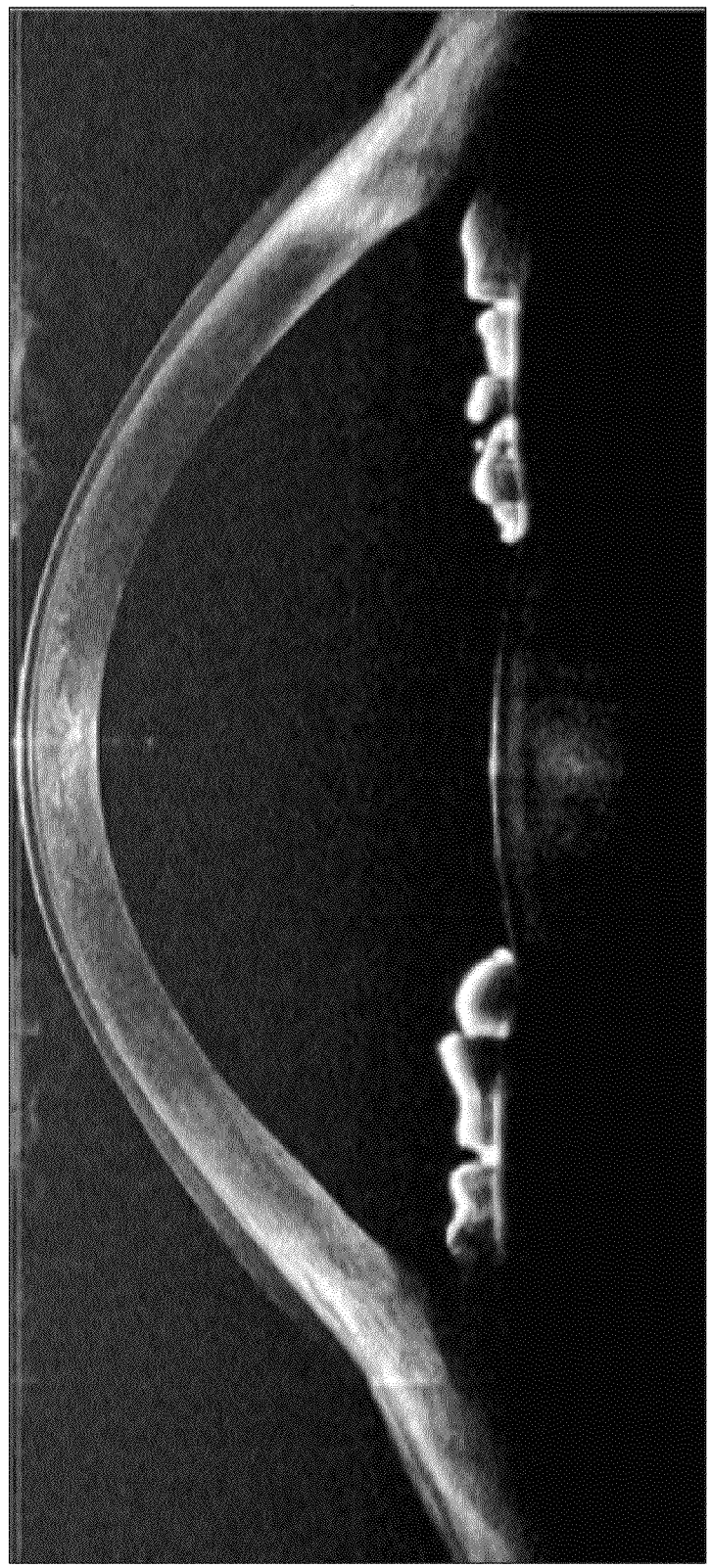
FIG. 2 is an image obtained using a full range anterior segment Spectral Domain Optical Coherence Tomography (SDOCT) system with a 7.5 mm depth of view with telecentric imaging optics.
Figure 3:
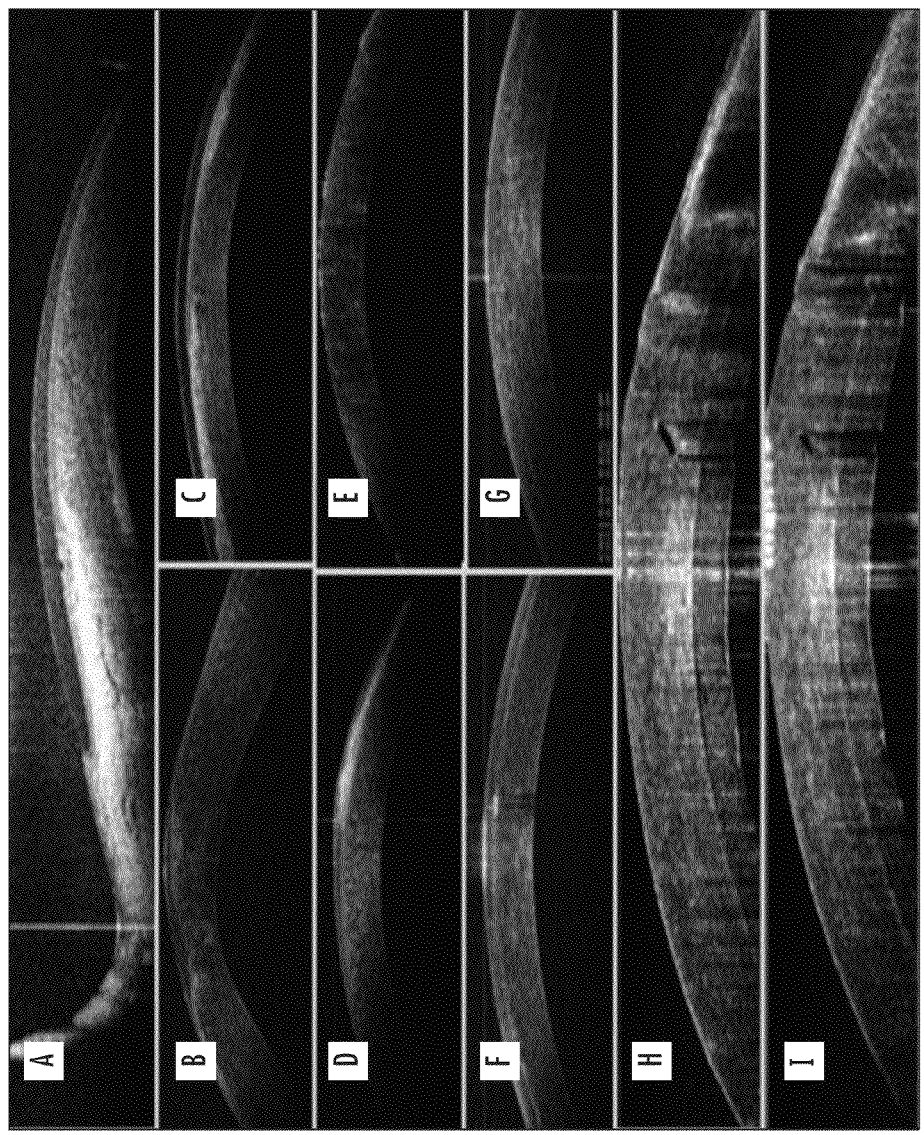
FIGS. 3A through 3I are a series of images obtained using a traditional SDOCT system with telecentric imaging optics.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Although many of the examples discussed herein refer to the sample being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

Some embodiments of the present inventive concept provide an imaging system that is more suited to clinically useful imaging of the cornea, the tear film, and the tissue ultrastructure of the inner eyelid, conjunctiva and sclera. Optics suited for imaging curved surfaces with a wide field of view are provided. To provide such a system, the following challenges have been address: (1) Invert the scanned focal field to match the surface of the cornea; (2) Equalize the optical path lengths so that a spherical surface is imaged to a plane at constant image depth; and (3) Introduce optical elements that allow such a design to be compact and cost effective.

Referring to FIGS. 4A-4C, the impact of field curvature and path length with respect to cornea curvature for three different models of cornea shape (A,B,C) will be discussed. The solid lines (left) are cornea shape, i.e. the shape that will be imaged by traditional telecentric OCT optics. The dashed lines (left) represent the focal field of the target optics.

In particular, FIGS. 4A-4C illustrate Aspheric OCT Scan Field Curvature vs. Cornea Shape. Telecentric imaging of cornea surface requires deep imaging for wide field of view (solid lines, left). Sphero-telecentric imaging reduces the required depth of view, and provides a surface image as a deviation from spherical (right). FIG. 4A illustrates a spherical cornea model, radius of curvature 7.5 mm; FIG. 4B illustrates a Spherical model with exponential tails; and FIG. 4C illustrates a keratonic model. The lines indicated the scanner field radius: 6 mm (----); 7.5 mm (--.--.--); 9 mm (--..--..--), respectively.

In traditional OCT the focal field will typically be flat or slightly curved upwards. There are at least two ways to achieve a focal field more adequately matched to outwardly curved surfaces with important ramifications. In one method, referred to herein as "Focal Inversion," aspheric optics are used to focus further along the z axis as a function of distance from the optical axis. The rays remain nominally telecentric. As used herein, "telecentric" refers to chief rays that remain substantially parallel to the originating optical axis. Using the Focal Inversion method, the resolution and image brightness at the target surface are substantially equalized, but the path lengths are not; the shape of the cornea may appear as with traditional OCT, but resolution and brightness across the field of view (FOV) will be improved. In the second method, referred to herein as "Sphero-Telecentricity," the scanning rays are directed normal to a target field surface, specifically to a spherical field surface. As used herein, "normal" refers to being perpendicular to the surface of the target sphere. In these embodiments, the beams would be normal to a target sphere and, therefore, there would be no refractive warping on passing through the target surface. However, the path lengths away from the optical axis could be severely elongated and the surface distortion unmanageable. In the ideal case, the path lengths are equal across the field. In such a perfectly Sphero-Telecentric OCT system, a spherical subject contour would appear as a flat surface at constant depth.

In FIGS. 4A-4C, the surfaced contours as imaged by a Sphero-Telecentric OCT system as graphed on the right for three model cornea shapes. A spherical cornea (FIG. 4A) with radius of curvature larger than the scanner field curvature would appear to curve upward. A cornea with radius of curvature smaller than the scanner field curvature would appear to curve downward. The shape illustrated in FIG. 4B is a slightly more realistic model of a healthy cornea and the FIG. 4C illustrates a keratoconic model. Thus, given a perfectly Sphero-Telecentric imaging system, the imaged shape of the cornea will be a direct map of the deviation from sphericity; imaged in three dimensions, this surface contour will lend itself to immediate decomposition into Zernike components. Furthermore, even for significant deviation from spherical, the entire surface of a cornea will map into a field depth half that of the telecentrically imaged subject, providing significant depth of field for tissue imaging and evaluation using a system, such as the Envisu R4300.

Figure 5A:
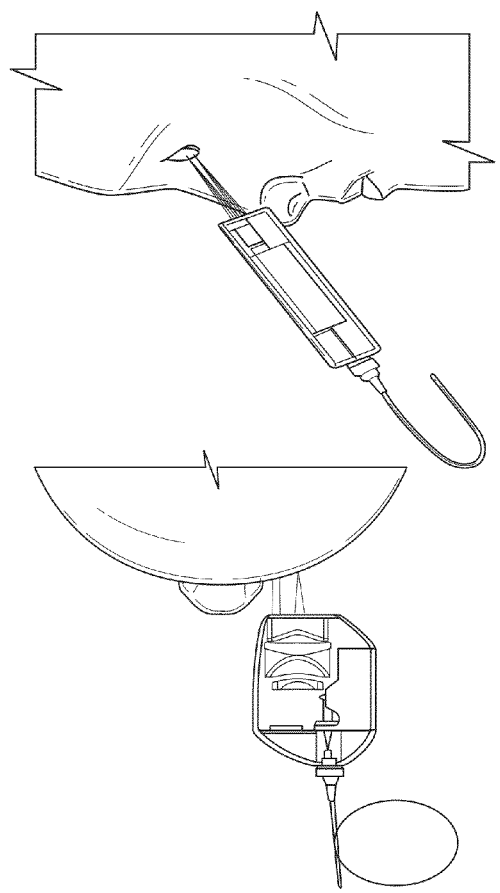
FIGS. 5A and 5B illustrate two optical scan head designs in accordance with some embodiments of the present inventive concept.
Figure 5B:
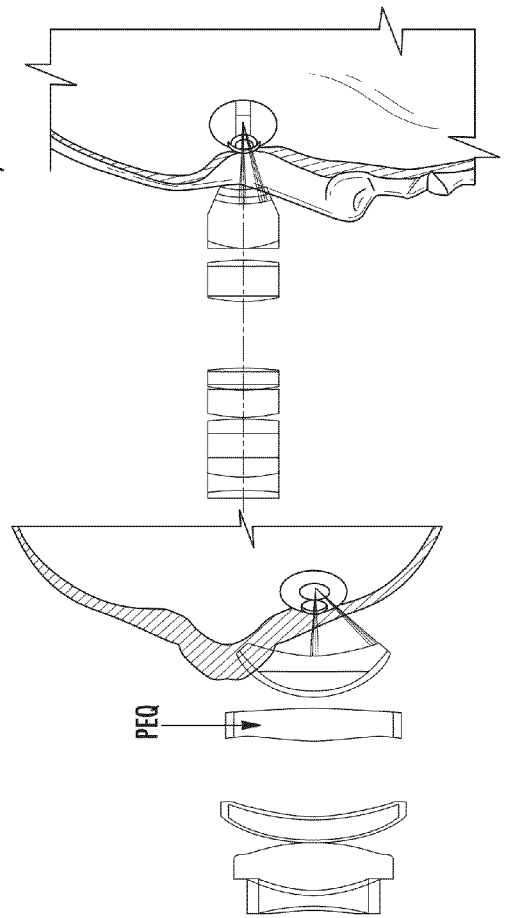

Referring now to FIGS. 5A-5B, two designs using aspheric optics are illustrated. For example, FIG. 5A illustrates a design using Focal Inversion and FIG. 5B illustrates a design using Sphero-Telecentricity. The associated performance parameters the aspheric head designs for FIGS. 5A and 5B are listed in Table 1 set out below.

TABLE 1

| Concept | Spot Size (um) Airy | RMS vs FOV (mm) 0 | 3 | 5 | 7 | 9 | OPL Variation (mm) | Working Distance (mm) | Device Length (cm) |
|---|---|---|---|---|---|---|---|---|---|
| Focal Inversion | 13 | 4 | — | 5 | — | 14 | 4.329 | 36 | 10 |
| Sphero_telecentric | 16 | 3 | 14 | 15 | 6 | — | 0.005 | 25 | 25 |

Referring to FIG. 5A, design 1 offers exceptional resolution across the surface of a cornea (5-15 μm) in an 18 mm field of view, and a compact package (10 cm in length). However, the path length variation across the field is 4.3 mm. This neither collapses a spherical target to a plane, nor is path length directly correlated to a useful function; the shape of the image cornea could be derived from calibration of the scanned field, but this introduces an additional complexity.

Referring to FIG. 5B, design 2 achieves the objective of path length equalized Sphero-Telecentricity. The path length variation across a 14 mm field of view is 5 μm (0.005 mm), which is exceptional. This is accomplished by an inventive use of aspheric imaging optics together with a novel shaped path equalizing element (PEQ). The resolution remains within 15 μm across the field. The trade-off is an increase in optical elements and device length, at 25 cm. Various embodiments of the present inventive concept will be discussed below with respect to the figures below.

Figure 6:
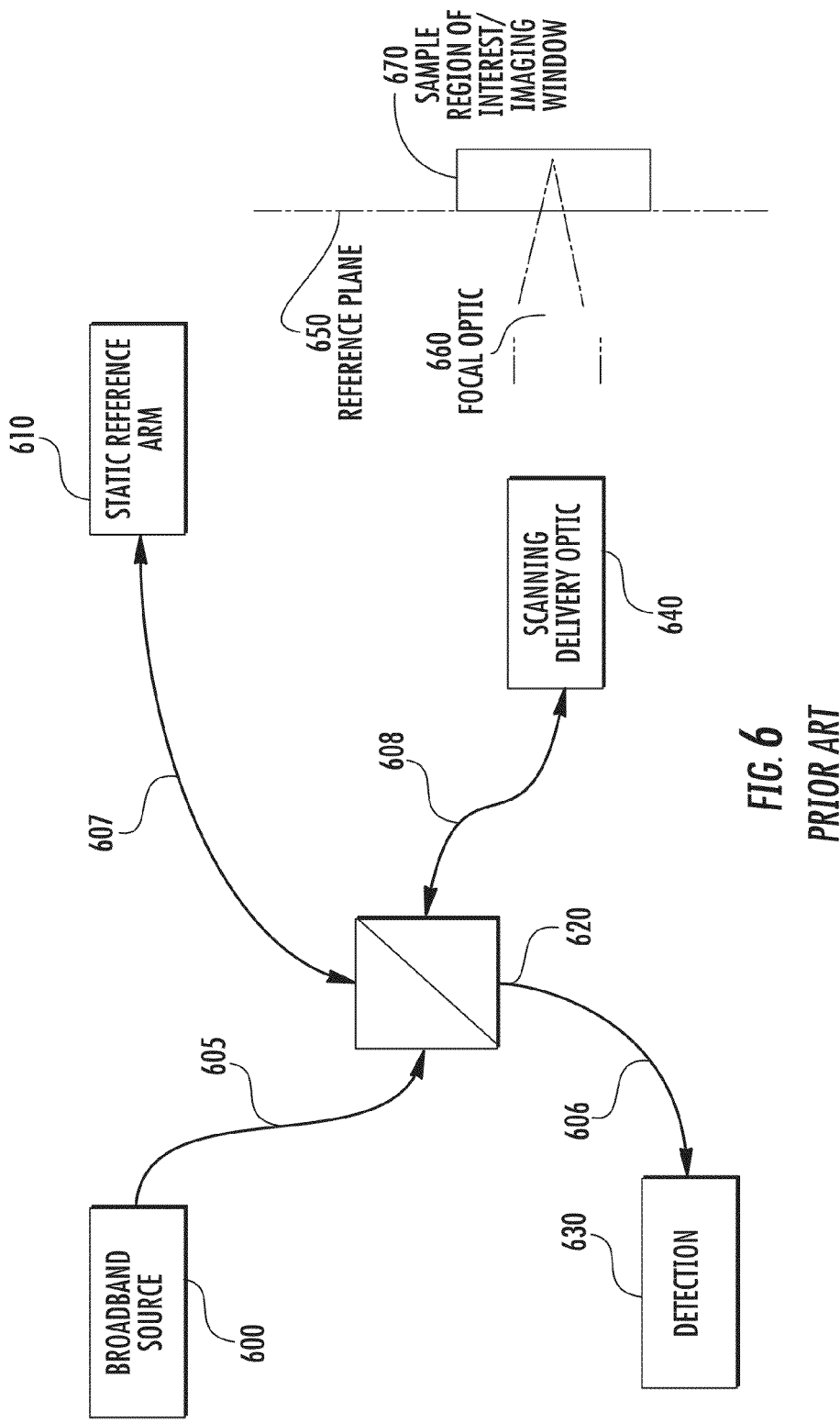
FIG. 6 is a block diagram illustrating an example OCT system.

FDOCT systems will now be discussed with respect to FIGS. 6 through 8 to provide some background related to these systems. Referring first to FIG. 6, a block diagram illustrating a Fourier domain OCT system will be discussed. As illustrated in FIG. 6, the system includes a broadband source 600, a reference arm 610 and a sample arm 640 coupled to each other by a beamsplitter 620. The beamsplitter 620 may be, for example, a fiber optic coupler or a bulk or micro-optic coupler without departing from the scope of the present invention. The beamsplitter 620 may provide from about a 50/50 to about a 90/10 split ratio. As further illustrated in FIG. 6, the beamsplitter 620 is also coupled to a wavelength or frequency sampled detection module 630 over a detection path 606 that may be provided by an optical fiber.

As further illustrated in FIG. 6, the source 600 is coupled to the beamsplitter 620 by a source path 605. The source 600 may be, for example, a SLED or tunable source. The reference arm 610 is coupled to the beamsplitter over a reference arm path 607. Similarly, the sample arm 640 is coupled to the beamsplitter 620 over the sample arm path 608. The source path 605, the reference arm path 607 and the sample arm path 608 may all be provided by optical fiber.

As further illustrated in FIG. 6, the sample arm 640 may include scanning delivery optics and focal optics 660. Also illustrated in FIG. 6 is the reference plane 650 and a representation of an OCT imaging window 670.

Figure 7:
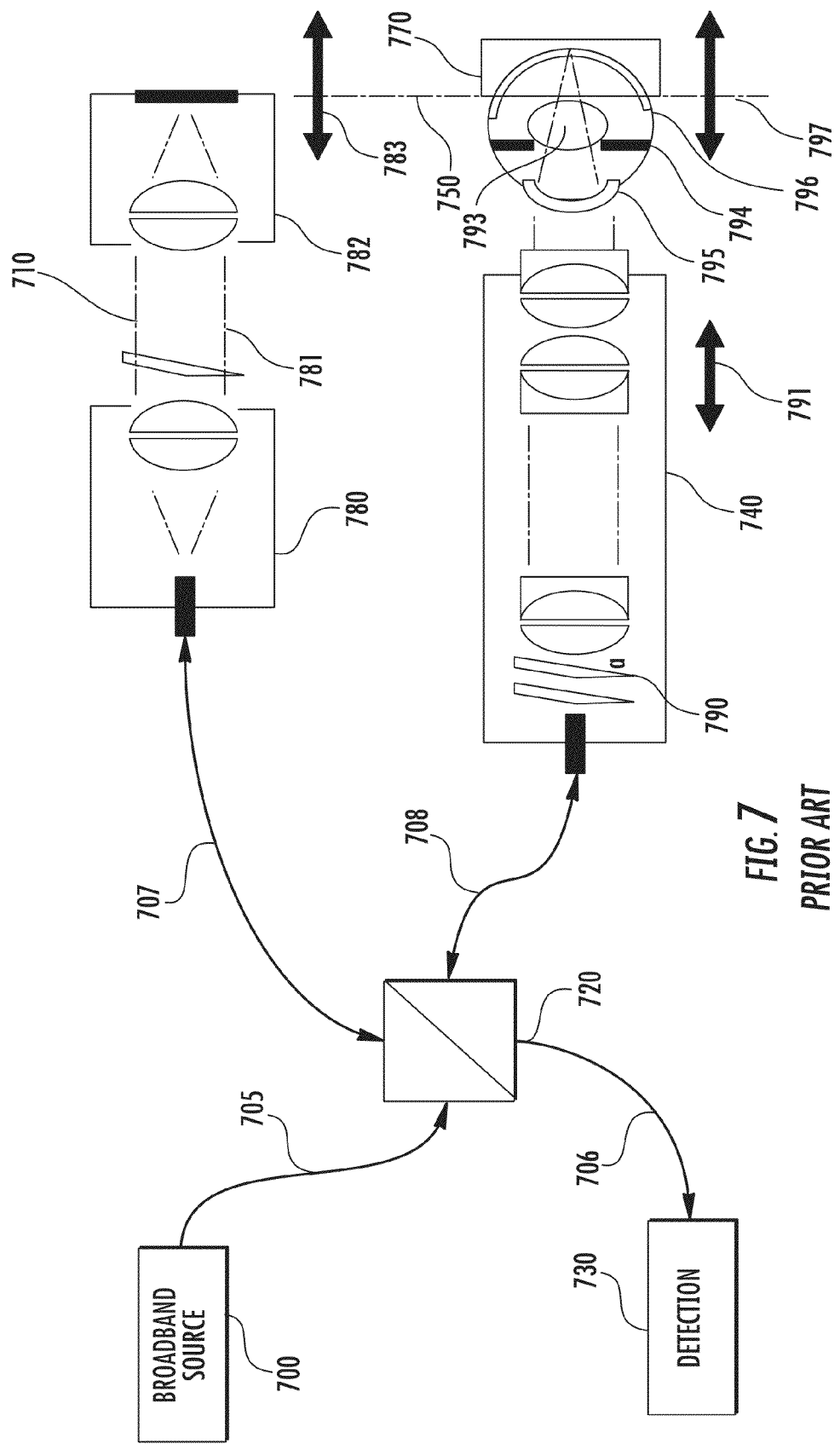
FIG. 7 is a block diagram illustrating an example OCT retinal imaging system.

Referring now to FIG. 7, a block diagram of an FDOCT retinal imaging system will be discussed. As illustrated in FIG. 7, in an FDOCT retinal imaging system, the reference arm 710 may further include a collimator assembly 780, a variable attenuator 781 that can be neutral density or variable aperture, a mirror assembly 782, a reference arm variable path length adjustment 783 and a path length matching position 750, i.e. optical path length reference to sample. As further illustrated, the sample arm 740 may include a dual-axis scanner assembly 790 and a variable focus objective lens 791.

The sample in FIG. 7 is an eye including a cornea 795, iris/pupil 794, ocular lens 793 and retina 796. A representation of an OCT imaging window 770 is illustrated near the retina 796. The retinal imaging system relies in the optics of the subject eye, notably cornea 795 and ocular lens 7, to image the posterior structures of the eye.

Figure 8:
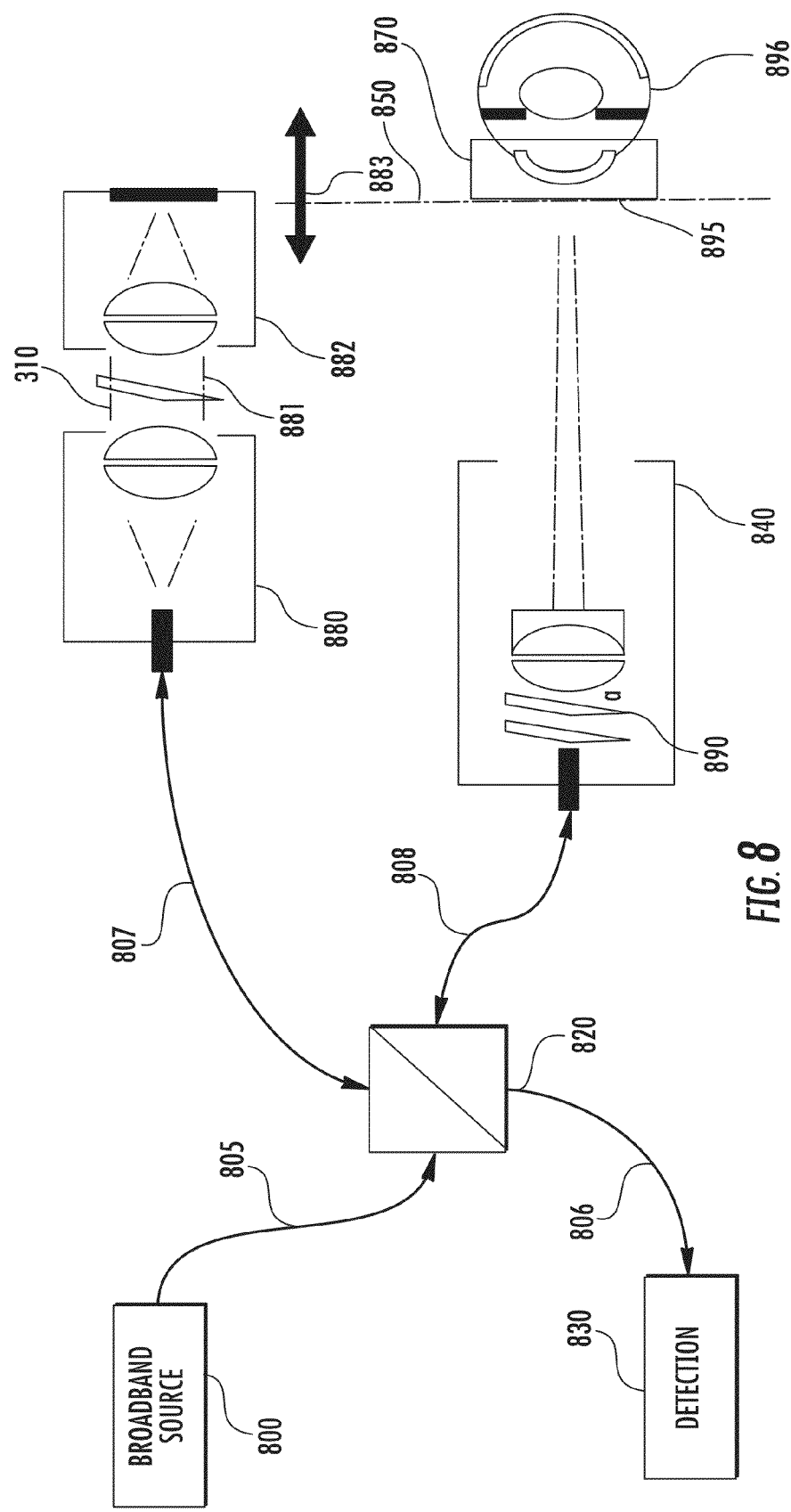
FIG. 8 is a block diagram illustrating an example OCT cornea imaging system.

Referring now to FIG. 8, a block diagram illustrating a FDOCT cornea imaging system will be discussed. As illustrated therein, the system of FIG. 8 is very similar to the system of FIG. 7. However, the objective lens variable focus need not be included, and is not included in FIG. 8. The anterior imaging system of FIG. 8 images the anterior structures directly, without reliance on the optics of the subject to focus on the anterior structures.

Figure 9:
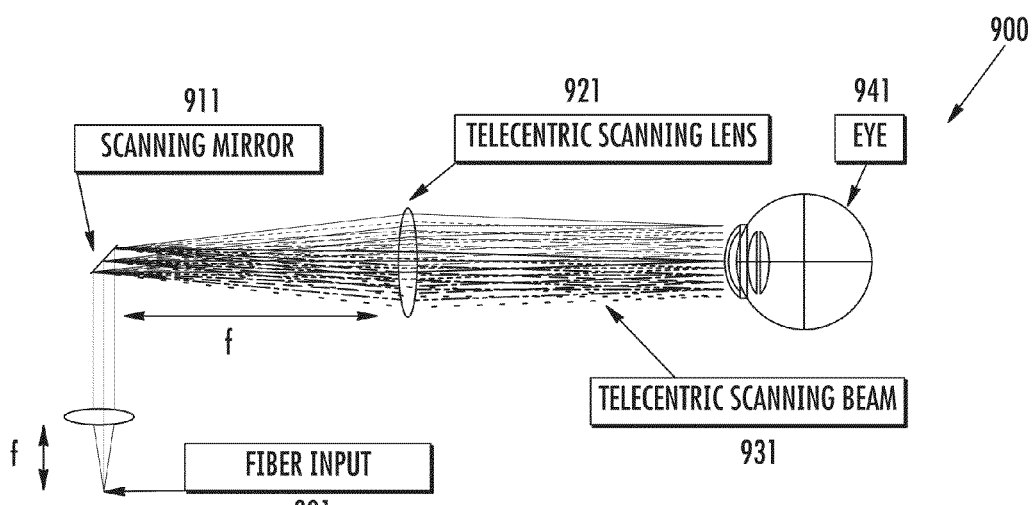
FIG. 9 is a block diagram illustrating a telecentric scanning system for ophthalmic anterior imaging.

Referring now to FIG. 9, a diagram illustrating a general concept of a telecentric scanning system for ophthalmic anterior imaging will be discussed. As illustrated in FIG. 9, the system 900 includes a fiber input 901, a scanning mirror 911, a telecentric scanning lens 921, telecentric scanning beams 931 that culminate at the sample, for example, and eye 941.

Figure 10:
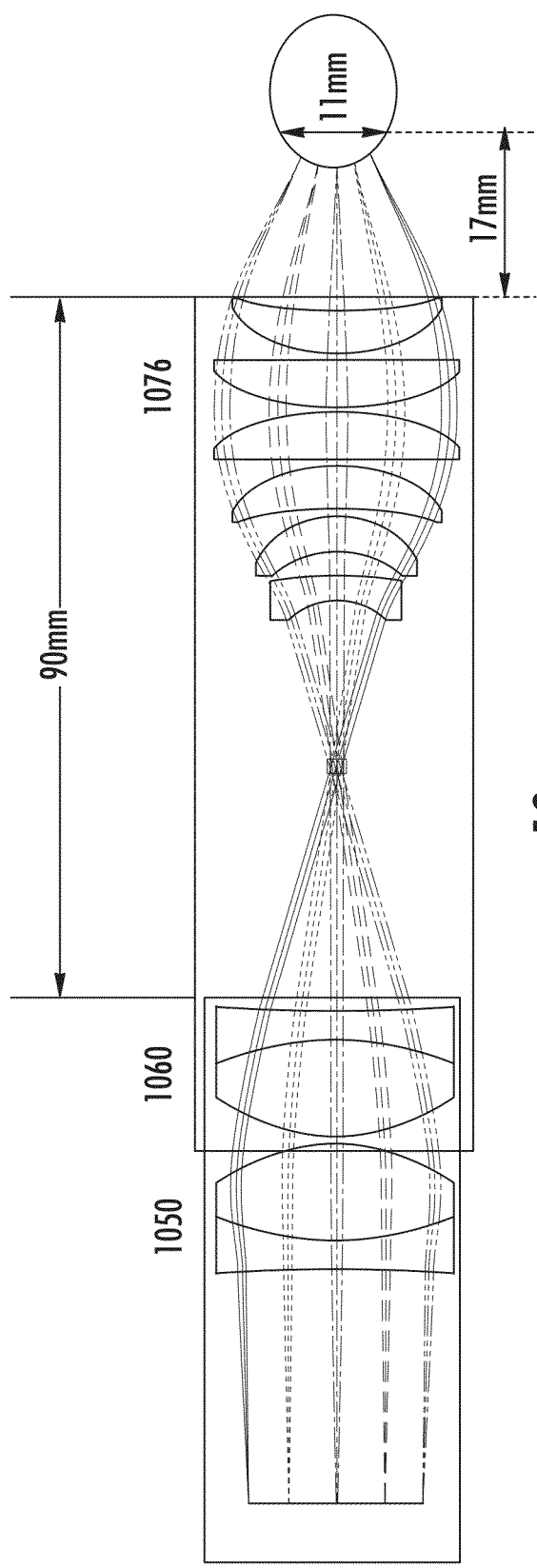
FIG. 10 is a block diagram illustrating a curved lens group for path-length managed imaging of a spherical surface (sphero-telecentric imaging).

Referring now to FIG. 10, a diagram illustrating a design of a curved lens group for path length managed imaging of a spherical surface (sphero-telecentric imaging) will be discussed. As illustrated in FIG. 10, the lens group includes an objective lens set 1050/1060 and a curved lens group 1076. As will be discussed further herein, the curved lens set 1076 may provide embodiments where the rays are more perpendicular to the surface of a curved sample. This may provide a stronger signal for layered structures, such as the cornea.

The system of FIG. 10 may essentially flatten the structure being imaged and, therefore, provide more detailed images within the readily achievable depth range of FDOCT systems. For example, the human eye does not have a uniform curvature. In particular, the diameters of portions of the eye may vary from about 8.0 mm (for the cornea) to about 12.0 mm (for the rest of the globe). The curved lens set 1076 illustrated in FIG. 10 may provide a lens designed to form a flat image of a curved object, for example, the human eye. The rays are normal to the curved surface to allow a zero optical path difference across the entire field of view. The curved lens set 1076 is configured to adapt to an existing retinal imager or OCT scanner to achieve cornea and OCT imaging in a flat plane. In other words, the curved lens set 1076 or multi-element lens may be configured to image a curved object, such as the surface of the cornea, onto a flat plane, such as the intermediate focus plane between the scanning and objective lenses.

Figure 11:
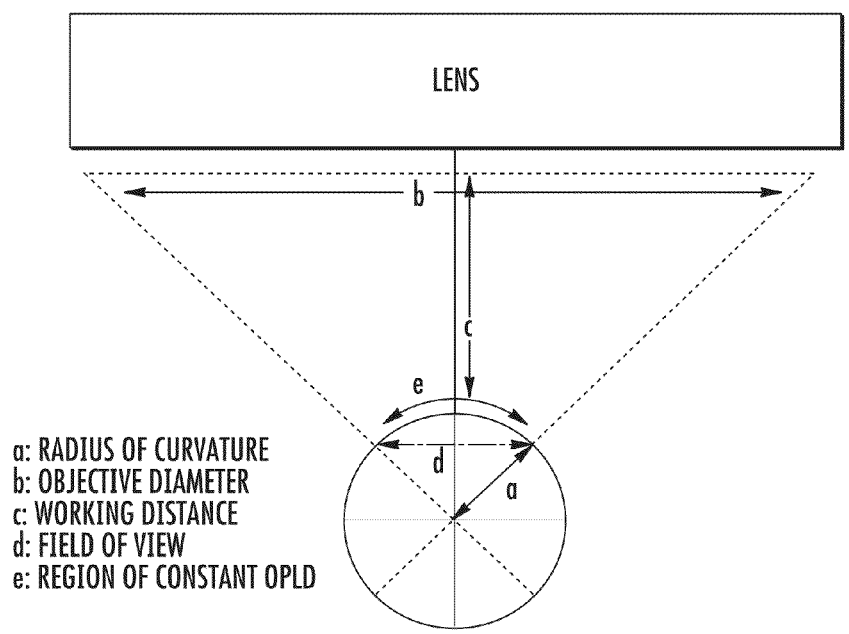
FIG. 11 is a block diagram illustrating imaging geometry for sphero-telecentric imaging in accordance with some embodiments of the present inventive concept.

Various embodiments of the present inventive concept will now be discussed with respect to FIGS. 11 through 31. Referring first to FIG. 11, a block diagram illustrating sphero-telecentric imaging in accordance with some embodiments of the present inventive concept will be discussed. As illustrated therein, imaging Geometry for sphero-telecentric imaging in accordance with some embodiment discussed herein has a radius of curvature (a), which is a target radius of curvature for imaging; an objective diameter of the lens (b) which provides a clear aperture of imaging objective; a working distance (c), which is the distance from imaging objective to surface of subject, for example, the apex of the cornea; a field of view (FOV) (s), which is angular extent or chord of the spherical surface to be imaged; and a region of constant optical path length distance (OPLD) (e), which is a sub region of the field of view over which optical path length uniformity is maintained.

Figure 12:
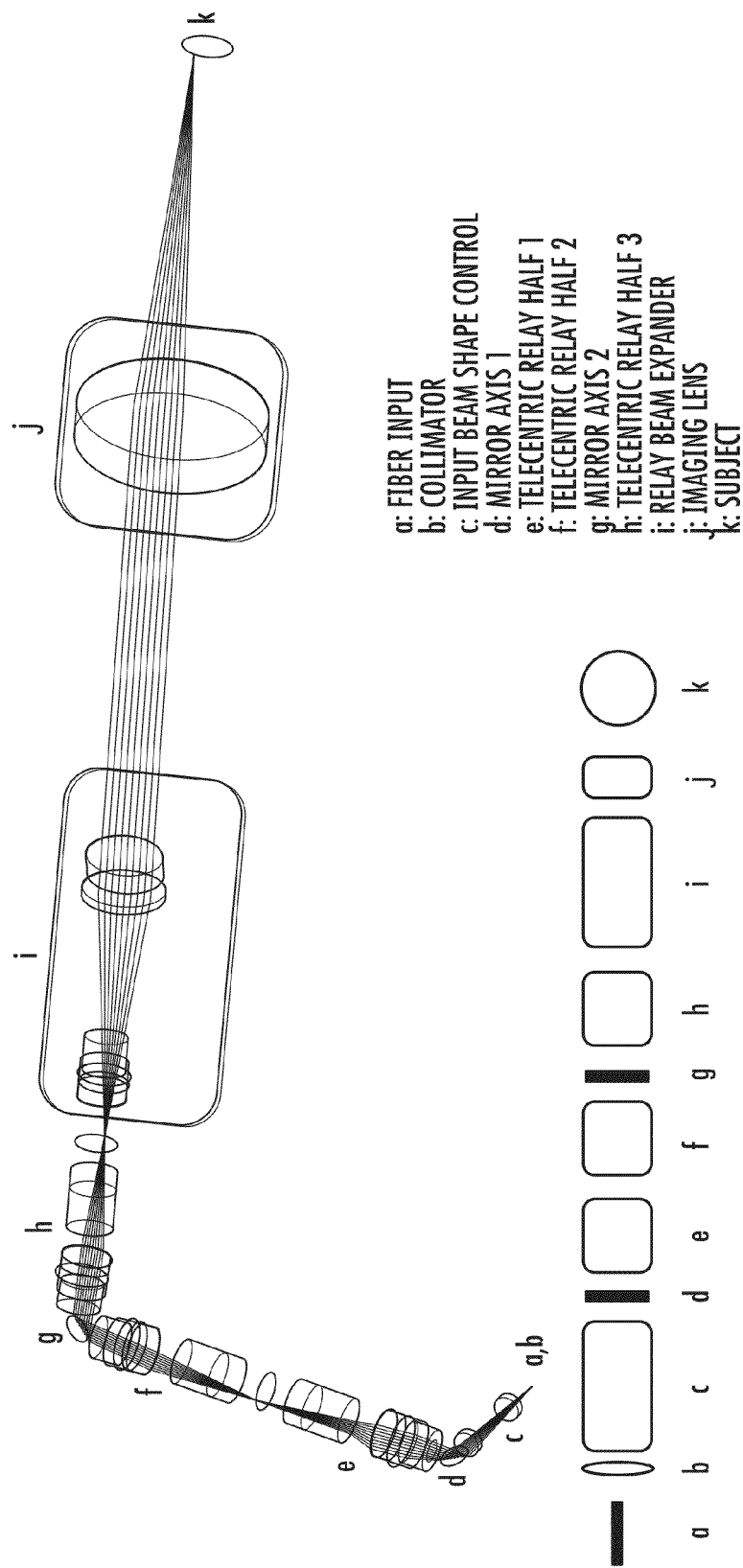
FIG. 12 is a diagram illustrating a telecentric scanning system with focus control, numerical aperture control and beam expansion in accordance with some embodiments of the present inventive concept.

Referring now to FIG. 12, a telecentric scanning system with focus control, numerical aperture (NA) control and beam expansion in accordance with some embodiments of the present inventive concept will be discussed. This system may provide for a highly telecentric surgical system, for example. As illustrated in FIG. 12, the telecentric imaging system includes a fiber input (a), which may include a single mode fiber; a collimator (b); an input beam zoom (input beam shape control), which provides the ability to adjust focus and control Numerical Aperture (NA); mirror axis 1 (d); a telecentric relay half 1 (e), which is a telecentric modified-Wild-eye-piece design; a telecentric relay half 2 (f), which is similar to (e); a mirror axis 2, orthogonal to mirror axis 1 (g); a telecentric relay half 3 (h), which is similar to (e); a telecentric beam expander (i); an imaging lens (j), which may be achromatic doublet; and a subject, which many be an eye.

Figure 13A:
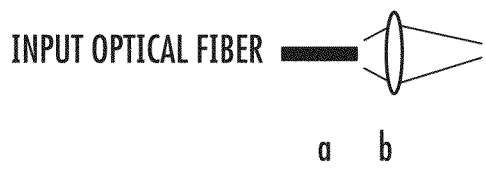
FIGS. 13A through 13C are a series of diagrams illustrating input beam shape control.
Figure 13B:
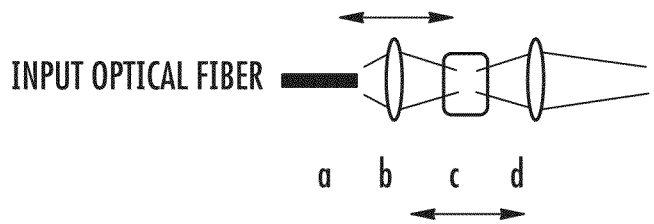
Figure 13C:
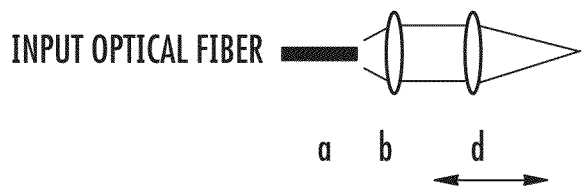

FIGS. 13A through 13C illustrate a series of diagrams illustrating an input beam zoom (IBZ) for input beam shape control. In particular, FIG. 13A illustrates a method of shaping the interrogating beam. As illustrated therein, the collimating lens that follows the input optical fiber is allowed to move away from collimation, indicated by the arrow a to b. This design is discussed in U.S. Pat. No. 7,843,572 to Tearney for an endoscopic delivery system. The movement of the collimating lens impacts both focus and numerical aperture of the beam delivery without enough degrees of freedom to shape the beam in a sufficiently controlled manner.

Referring now to FIG. 13B, as illustrated therein, a second moveable negative lens is added after the first movable positive lens. The arrangement illustrated in FIGS. 13B improves the separation of focus and numerical aperture. However, allowing movement of the initial collimating lens in this set up adversely impacts aberrations in the downstream system and may modulate the radiant power in the system, particularly if a small aperture truncates the beam originating in the source or source fiber.

Referring now to FIG. 13C, as illustrated therein, a fixed collimated beam is used followed by a moveable positive lens. In this embodiment, only the position of the focus can be changed, there is no effect on the NA.

Figure 14A:
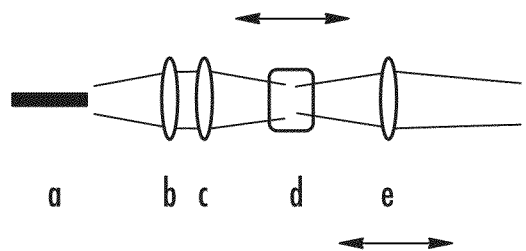
FIGS. 14A and 14B are a series of diagrams illustrating input beam shape control in accordance with some embodiments of the present inventive concept.
Figure 14B:
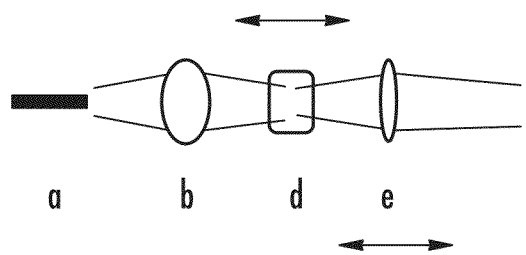

FIGS. 14A and 14B are a series of diagrams illustrating input beam shape control in accordance with some embodiments of the present inventive concept. Some embodiments of the present inventive concept provide a focal system that addresses the issues discussed above with respect to FIGS. 13A through 13C in providing constant radiant power to the downstream system, and sufficient degrees of freedom to independently control numerical aperture (NA) and focus.

Referring first to FIG. 14A, an input source or source fiber (a) is followed by a first positive lens (b) positioned nominally one focal length away from the source, thus collimating the source. The first positive lens (b) is followed by a second positive lens (c) that provides a first focal power to the system. The second positive lens (c) is followed by a third lens (d) that is a movable negative lens that modifies the power of the second positive lens (c). The negative lens (d) is followed by a fourth lens (e), which is a movable positive lens that controls the final output of this multi-lens system.

Further embodiments of the present inventive concept provide a lens grouping that acts a zoom system, providing magnification or demagnification of the image of the source or source fiber into the downstream optical system. Referring to FIG. 14B, the single mode fiber (a) is followed by a first lens system (b) having an input NA and an exit NA and input focal length and output focal length. The first lens system (b) is followed by movable negative lens system (d), which followed by movable positive lens system (e). In one configuration the output of the input beam zoom is a collimated beam that is focused by downstream optical elements. Through coordinated movement of the negative lens system (d) and the final positive lens system (e), the numerical aperture of the complete system may be modified without modifying the degree of collimation or focus. From any such numerical aperture state, a modified focal state may be achieved by independent movement of the final lens, the focus is modified. It will be understood that the method of setting numerical aperture and focus need not follow the sequential adjustment discussed above. For example a lookup table may be used to select the positions of the lens systems to achieve a desired combined output state. It will also be understood that in some embodiments, the lens system (b) of FIG. 14B may be substantially equivalent to the first and second positive lenses (b and c) of FIG. 14A, and conversely that lens systems (d) and (e) may not be lens singlets but may be more complex lenses or groups of lenses.

Referring now to FIGS. 15A through 15C, a series of block diagrams illustrating diagrams of lens positions for beam shape control for high numerical aperture, low numerical aperture and low numerical aperture with deep focus, respectively, in accordance with some embodiments of the present inventive concept will be discussed. As illustrated in FIGS. 15A through 15C, Lens (a) is the first positive lens; lens (b) is the second negative lens; and lens (c) is the third positive lens. The distance between lens (a) and lens (b) will be referred to as the first lens spacing (D1) and the distance between lens (c) and lens (b) will be referred to as the second lens spacing (D2). The position of the lens (a) is fixed in all of FIGS. 15A through 15C. Similarly, lens (b) and lens (c) are both moveable in all of FIGS. 15A through 15C.

FIG. 15A illustrates embodiments for a high numerical aperture imaging system. The zoom controls the numerical aperture of the system; in a collimated application, where the final focus is determined by downstream optics, the zoom magnification provides a magnification between the entrance pupil and exit pupil. The larger this magnification, the greater the numerical aperture of the final imaging system. FIG. 15B illustrates embodiments having a low numerical aperture, the first spacing D1 has increased and the second spacing D2 has decreased. FIG. 15C illustrates embodiments having a low numerical aperture and deeper focus, the second spacing D2 has further decreased and the system has been modified from a collimated state to a diverging state.

Figure 16:
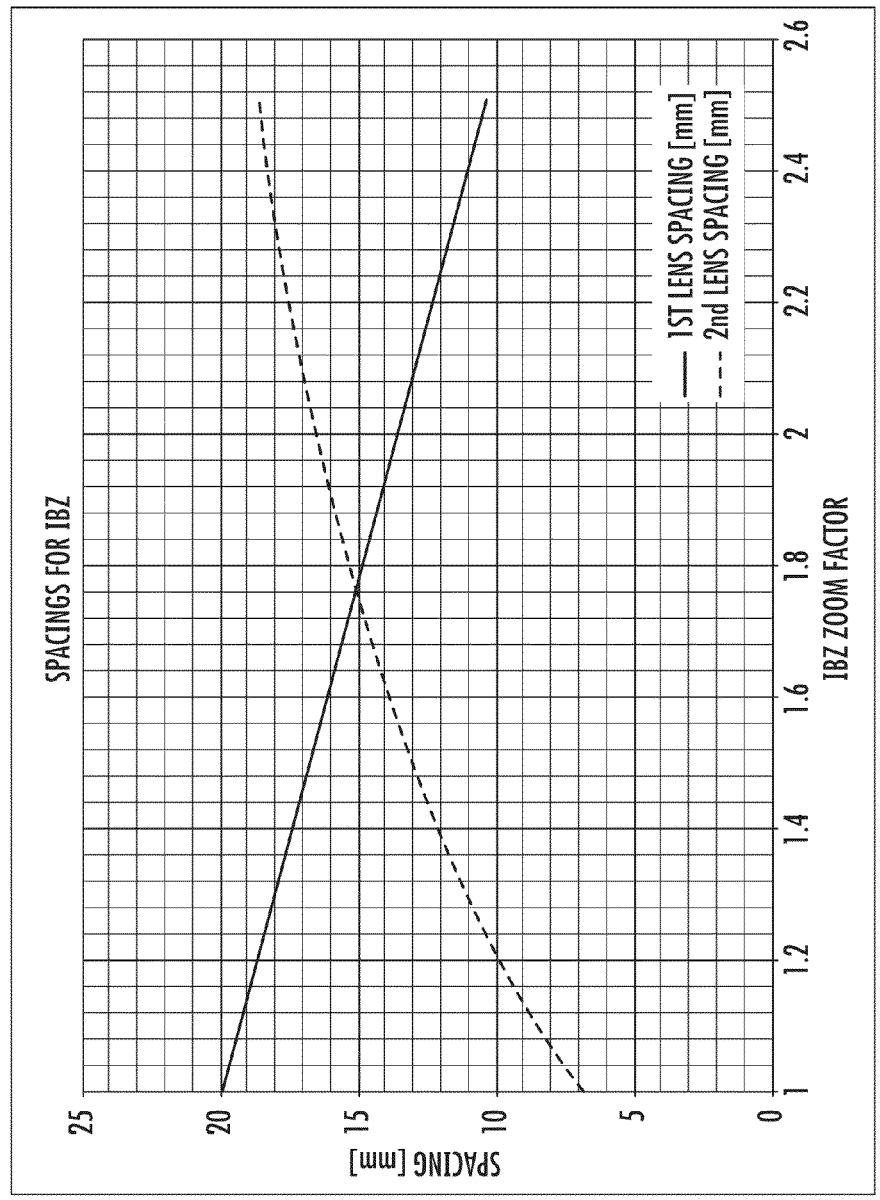
FIG. 16 is a graph illustrating zoom factor as a function of input beam zoom lens spacing in accordance with some embodiments of the present inventive concept.

Referring not to FIG. 16, a graph illustrating zoom factor as a function of input beam zoom (IBZ) lens spacing in accordance with some embodiments of the present inventive concept will be discussed. As used herein, the "input beam zoom" refers to the zoom factor as a function of first and second lens spacing, D1 and D2 discussed with respect to FIG. 15A through 15C. The zoom factor controls the numerical aperture (NA). For example, at zoom factor=1, the system is in low NA mode. As zoom factor increases, the NA of the system increases. As discussed above, the first lens spacing (D1) is the distance to the negative lens from the first positive lens and the second lens spacing (D2) is the distance to the final positive lens from the negative lens.

Figure 17:
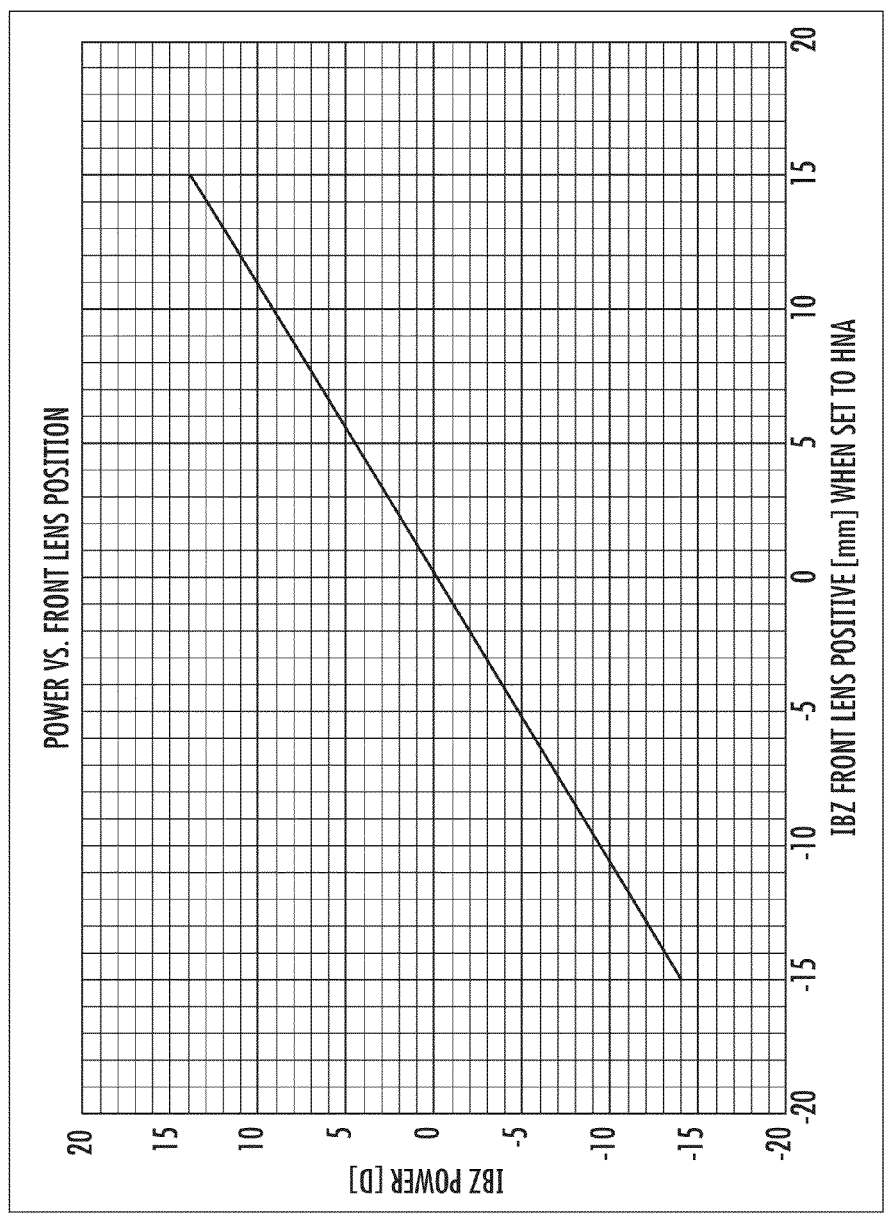
FIG. 17 is a graph illustrating input beam zoom focal power as a function of final lens spacing in accordance with some embodiments of the present inventive concept.

Referring now to FIG. 17, a graph illustrating IBZ focal power as a function of final lens spacing in accordance with some embodiments of the present inventive concept will be discussed. At any zoom setting, focus may be adjusted by movement of the final lens of the IBZ (lens c of FIGS. 15A through 15C). Increasing the second lens spacing (D2) increases the focal power of the IBZ, and shortens the focal length of the system. Reducing the second lens spacing (D2) reduces the focal power of the IBZ and increases the focal length of the system. It will be noted that two degrees of freedom, lens spacing D1 and lens spacing D2, provide a continuous range of control of system numerical aperture and focus. The range of control is dependent on the available physical space for movement of the lenses, the respective powers of the lenses, and the downstream imaging optics, as will be understood by one skilled in the art. It will also be noted that the imaging conditions are deterministic, and multiple modes of control may be employed to achieve a desired state, including without limitation, sequential or simultaneous movement of lens, movement according to values set in a lookup table, or adjustment with feedback based on positional encoders or in response to image quality feedback.

Figure 18:
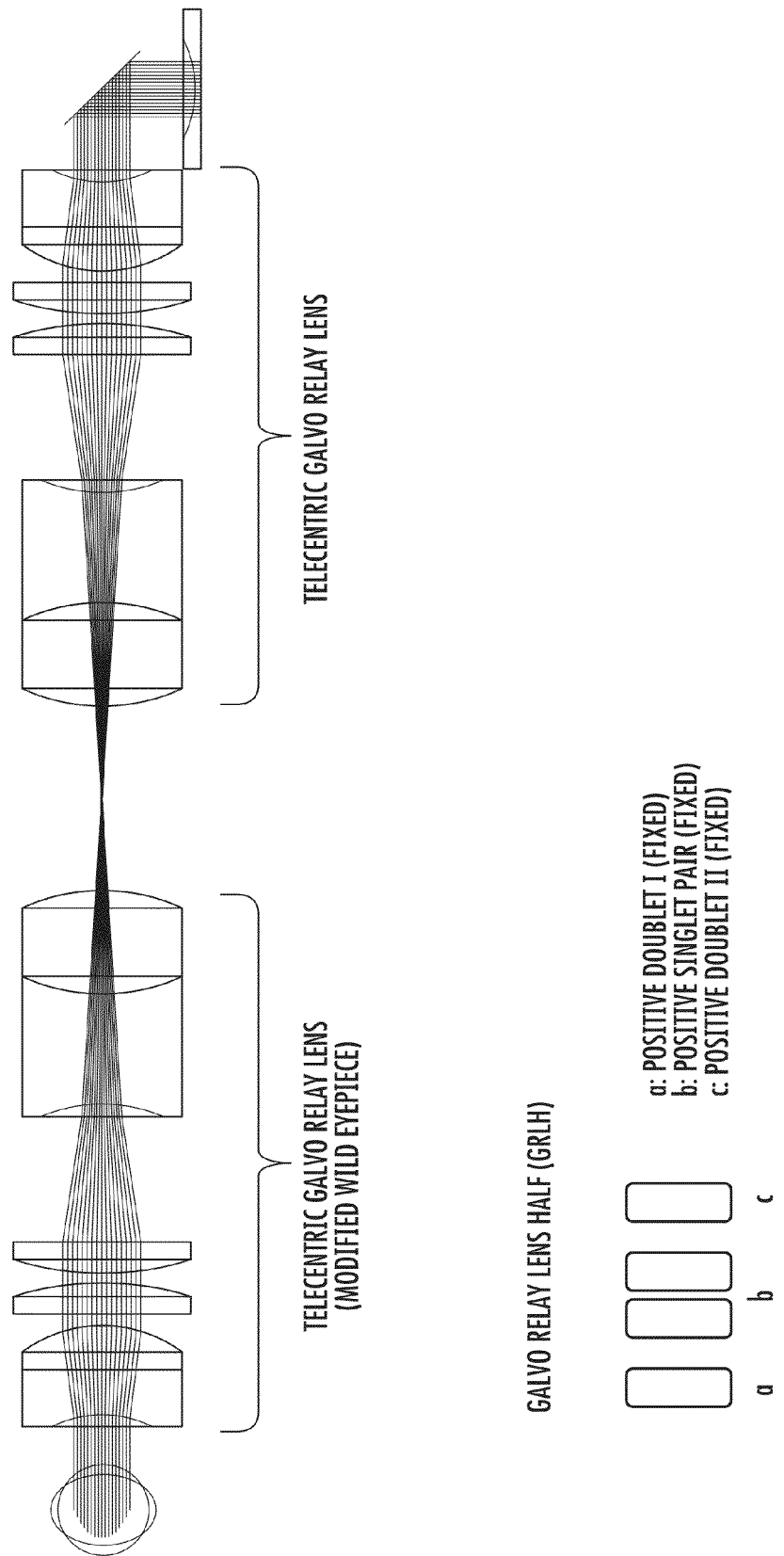
FIG. 18 is a diagram illustrating a galvo relay lens (GRL) system in accordance with some embodiments of the present inventive concept.

Referring now to FIG. 18, a diagram illustrating a galvo relay lens (GRL) system in accordance with some embodiments of the present inventive concept will be discussed. As illustrated therein, the system includes a two telecentric GRLs (modified Wild eyepiece), i.e. a first GRL half (GRLH) and a second GRLH. Each GRLH includes a first positive doublet (a) that is fixed, a positive singlet pair (b) that is fixed and a second positive doublet (c) that is fixed. The GRLs control the telecentricity of the system. The GRL as proposed enables a very high degree of telecentricity along two orthogonal axis. This telecentricity has not been deployed previously in scanning beam ophthalmic imaging systems.

Figure 19:
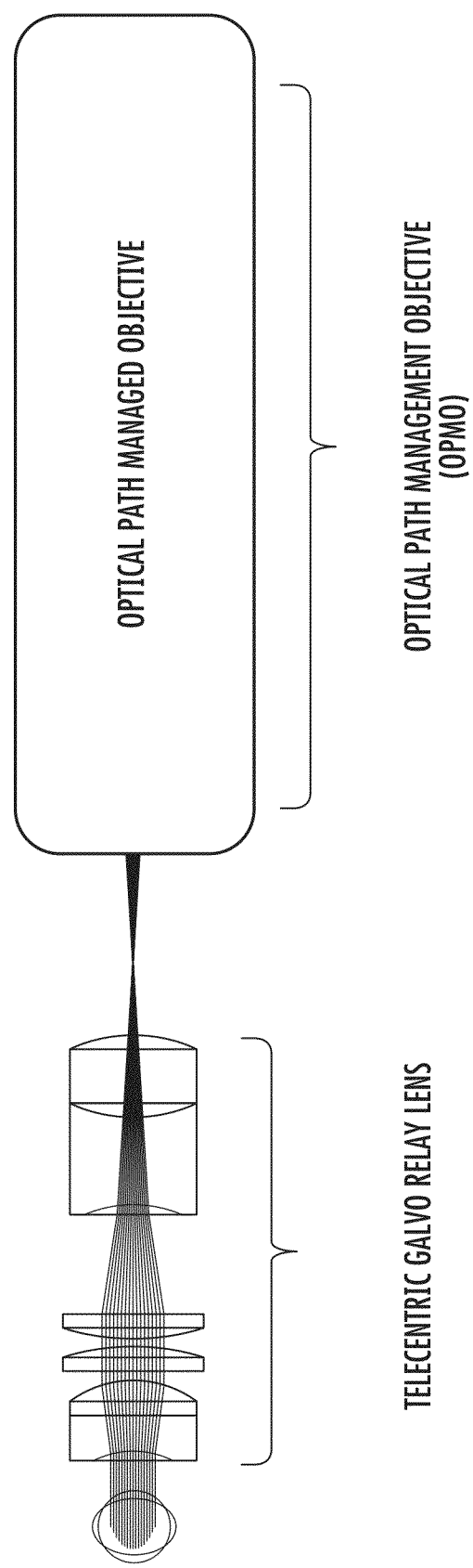
FIG. 19 is a block diagram illustrating an optical path length and telecentricity manager in accordance with some embodiments of the present inventive concept.

Referring now to FIG. 19, a block diagram illustrating an optical path length and telecentricity manager in accordance with some embodiments of the present inventive concept will be discussed. As illustrated in FIG. 19, in some embodiments of the present inventive concept, an optical path management objective (sphero-telecentric objective) (OPMO) is introduced in the system after the final GRL.

Figure 20:
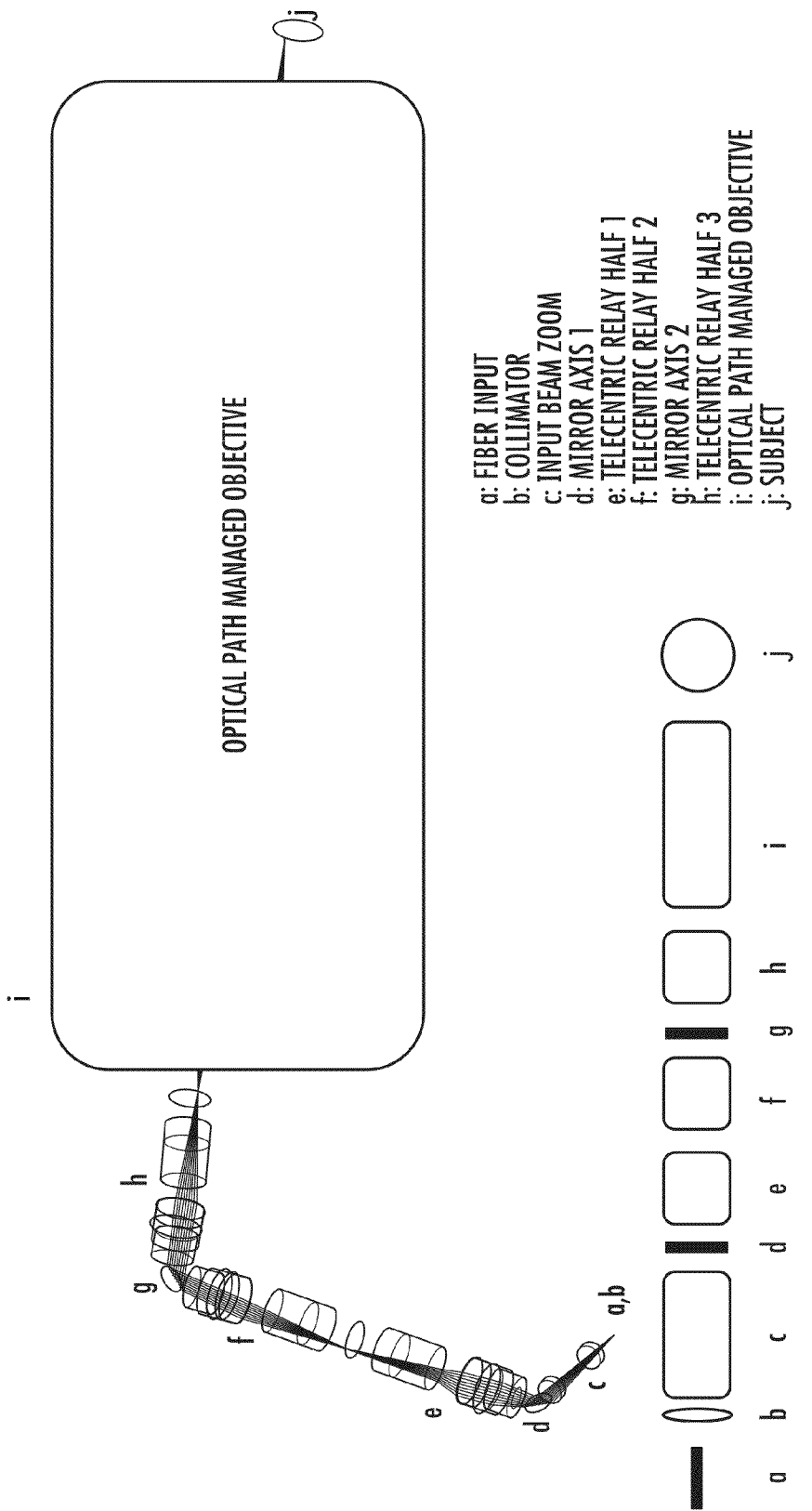
FIG. 20 is a block diagram of a telecentricity-managed OCT imaging path in accordance with some embodiments of the present inventive concept.

Referring now to FIG. 20, a block diagram of a telecentricity-managed OCT imaging path including an OPMO in accordance with some embodiments of the present inventive concept will be discussed. As illustrated in FIG. 20, the system includes a fiber input (a); a collimator (b); an input beam zoom (c); a mirror axis 1 scanning a long a first axis (d); a telecentric relay half 1 (e); a telecentric relay half 2 (f); a mirror axis 2 scanning along a second axis orthogonal to the first (g); a telecentric relay half 3 (h); an optical path managed objective (OPMP) (i); and a subject (j).

Figure 21:
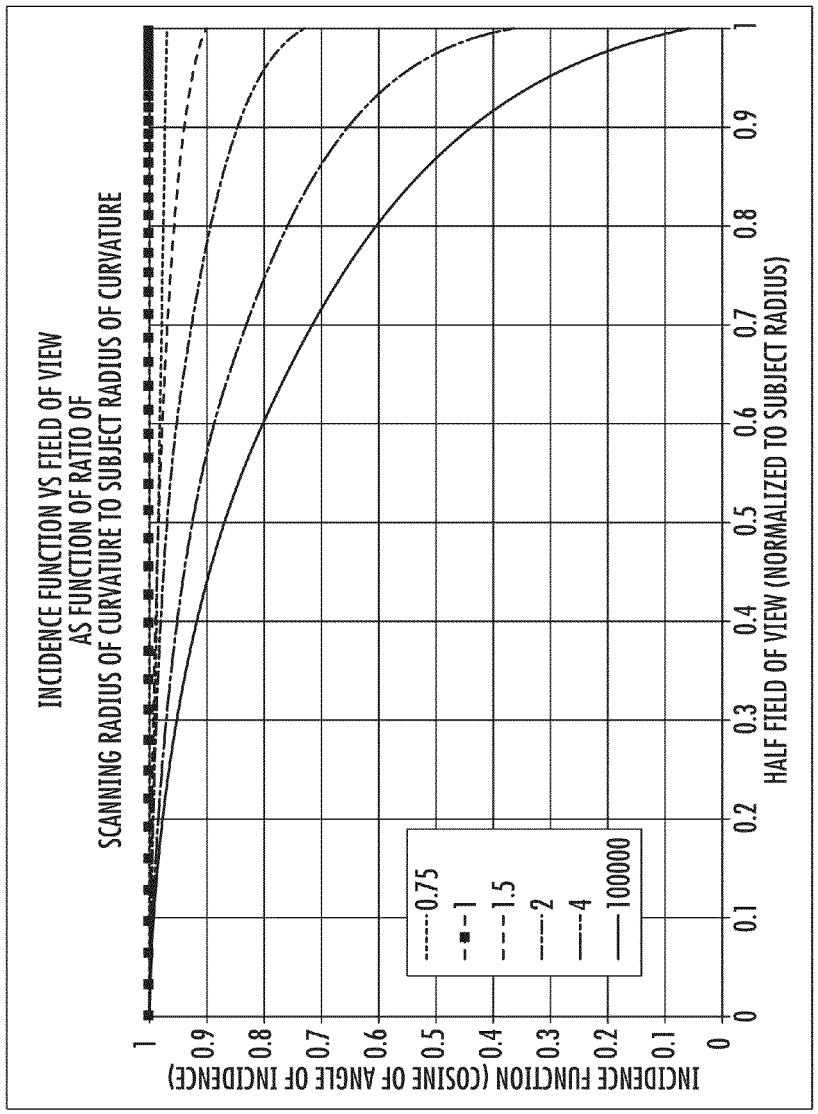
FIGS. 21 is a graph illustrating sphero-telecentricity in OCT imaging in accordance with some embodiments of the present inventive concept.

Referring now to FIG. 21, a graph illustrating spherotelecentricity in OCT imaging in accordance with some embodiments of the present inventive concept will be discussed. A sphero-telecentric imaging objective will focus normal to a spherical surface with a target radius of curvature. A Path-Managed sphero-telecentric objective for OCT imaging may ensure that the optical path length will be constant across the field of view (FOV) along the target radius of curvature.

It will be understood that it is not necessarily either desirable or possible to perfectly match the curvature of a human eye. First, the cornea of a human eye is not perfectly spherical. Second, it is desirable to avoid specular reflections that arise in true normal imaging of the air-to-cornea interface, The normal eye has a nominal radius of curvature of about 8 mm at the apex, increasing towards the limbus. In some embodiments of the present inventive concept, an imaging system is provided have a 16 mm radius of curvature, or 2 times the nominal apical radius of curvature. A radius of curvature larger than the apical radius of curvature of the cornea is chosen to allow a large field of view (FOV) with a comfortable working distance and an objective diameter that does not interfere with the subject physiology, for example, the brow or the nose of the subject.

Referring to FIG. 21, the cosine of the angle of incidence of the interrogating beam onto the cornea is plotted as a function of the position along the half field of view, normalized to the cornea radius, for different values of the ratio of the imaging radius of curvature to the cornea radius of curvature. In some embodiments of the present inventive concept, the imaging radius of curvature may be equal to or greater than the apical cornea radius. In particular, the imaging radius of curvature may be between about 1× and about 4× the apical radius of curvature of the cornea, or between about 1.5× and about 3× the apical radius of curvature of the cornea in order to optimize the trade-offs discussed.

Figure 22A:
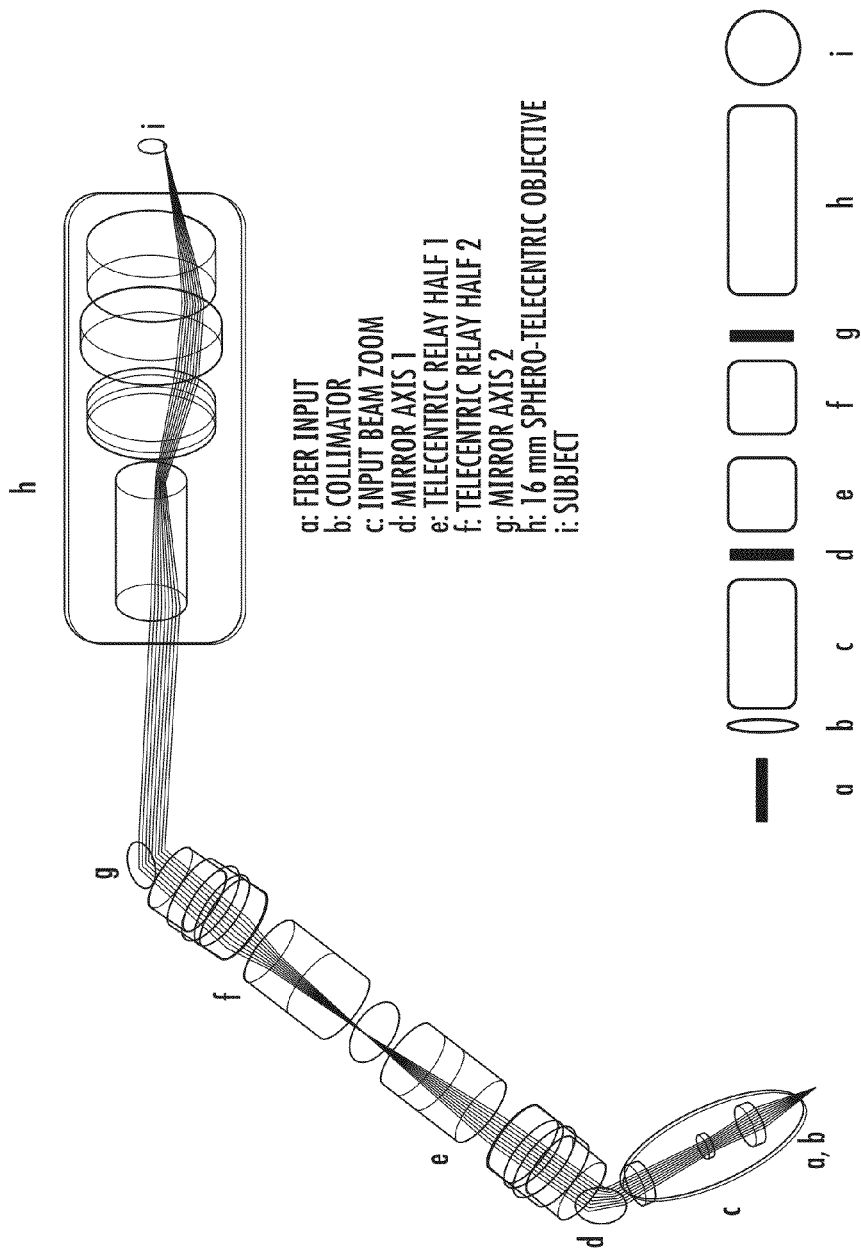
FIGS. 22A through 22C are diagrams illustrating elements of sphero-telecentric systems having a 16 mm radius of curvature in accordance with some embodiments of the present inventive concept.
Figure 22B:
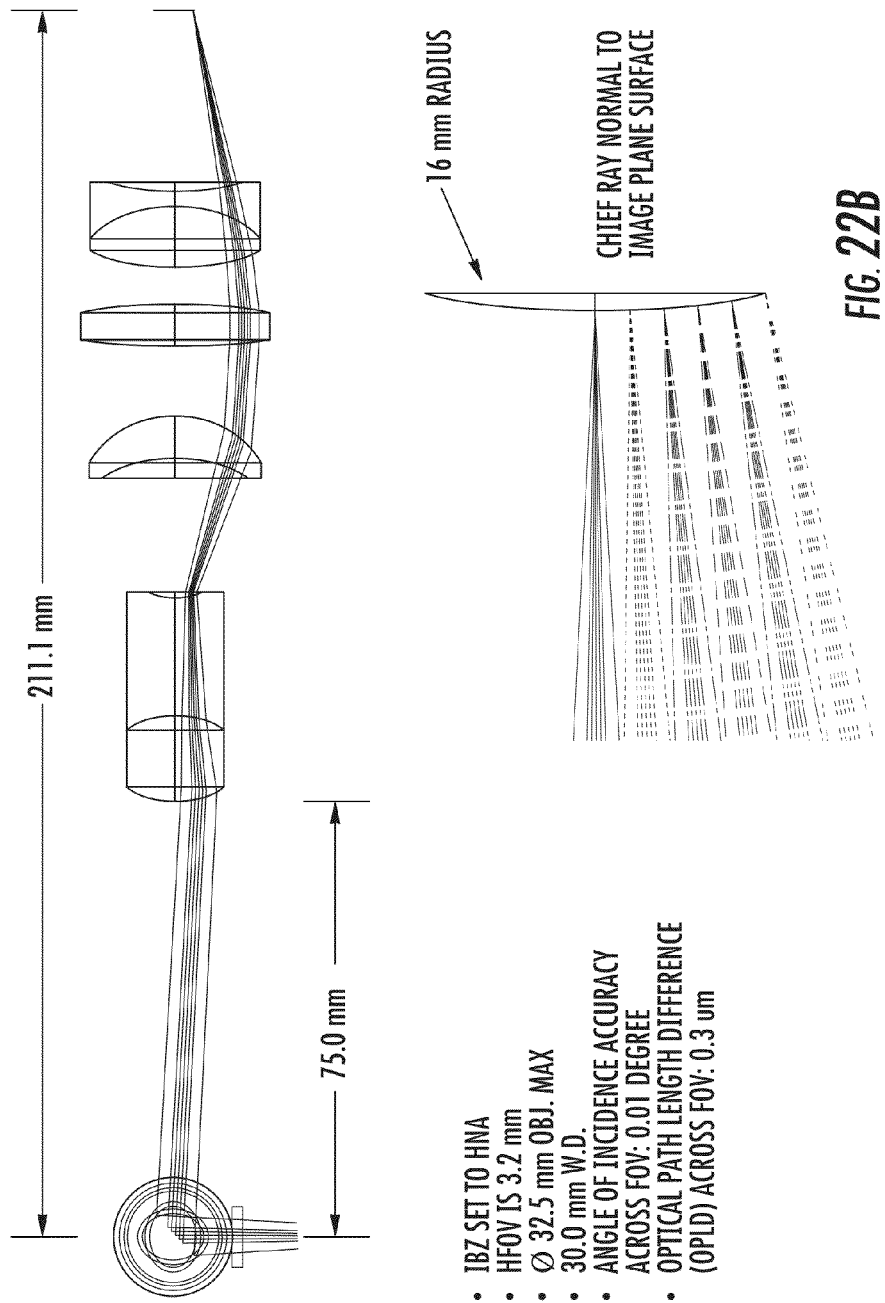
Figure 22C:
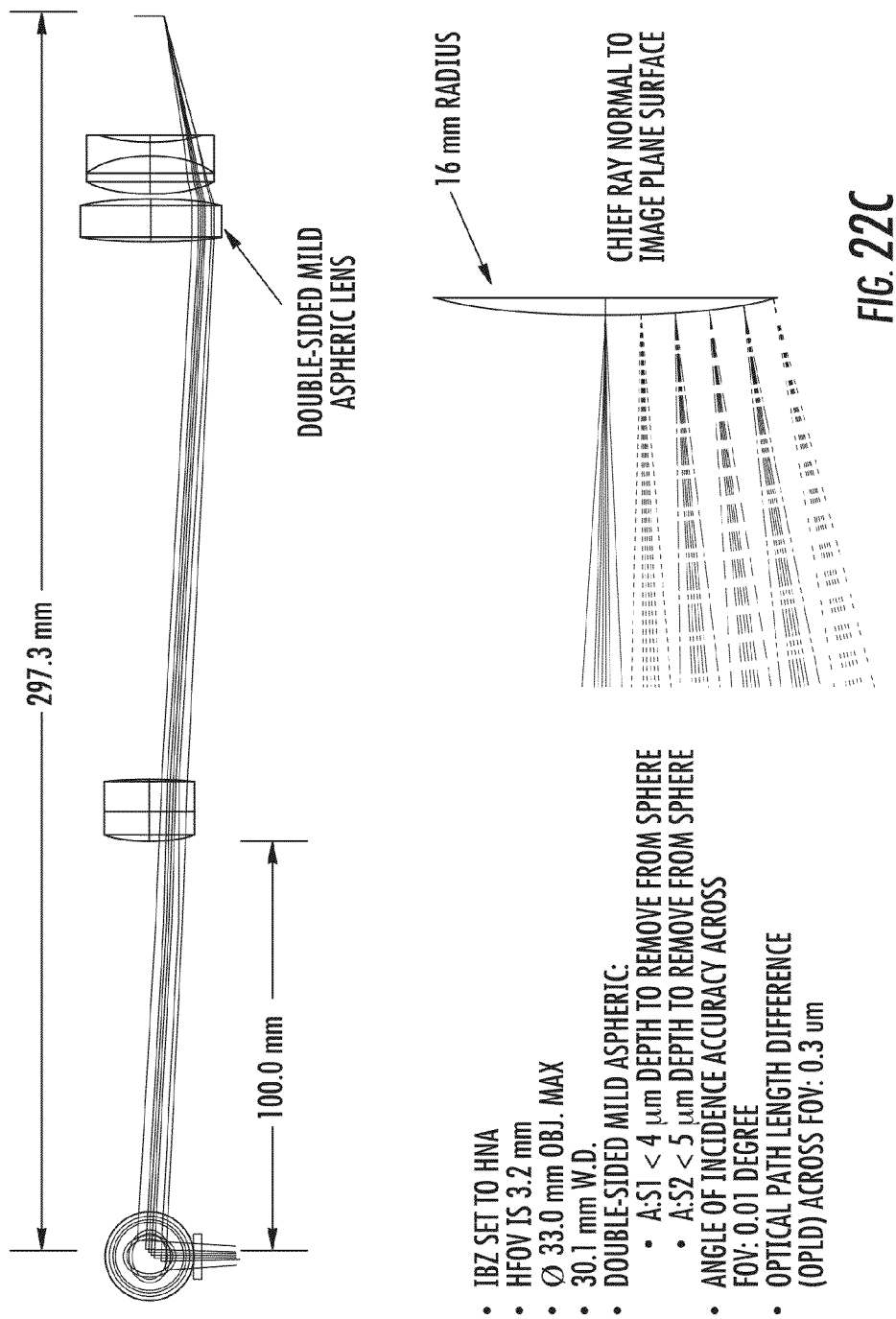

Referring now to FIGS. 22A through 22C, diagrams illustrating a sphero-telecentric system having a 16 mm radius of curvature in accordance with some embodiments of the present inventive concept will be discussed. As illustrated in FIG. 22A, the sphero-telecentric system includes a fiber input (a); a collimator (b); an input beam zoom (c); a mirror axis 1 (d); a telecentric relay half 1 (e); telecentric relay half 2 (f); a mirror axis 2 (g); a 16 mm sphero-telecentric objective (h); and a subject (i). In some embodiments of the present inventive concept, the sphero-telecentric imaging system may include a collimated (a) source followed by an input beam zoom (IBZ) (b). The beam images on a first galvo mirror (d) will scan in one direction. The first galvo (e) is telecentrically imaged onto a second galvo (f) that will scan in a second orthogonal direction. The input source is then imaged on the subject using the path-managed sphero-telecentric objective (h).

Referring now to FIG. 22B, embodiments of the 16 mm sphero-telecentric objective (h) of FIG. 22A using spherical optics will be discussed. As illustrated therein, the objective (h) includes four groups of optics in embodiments illustrated in FIG. 22B. The sphero-telecentric objective imaging to a 16 mm radius of curvature over a 6.4 mm field of view is prescribed using spherical (normal glass) optics. The four groups include a first doublet followed by a pair of singlets and a final doublet. The working distance (final lens to cornea) is 30 mm. The maximum diameter of the objective is 32.5 mm. The system images to an angle accuracy of 0.01 degree, with an optical path length consistent to 0.3 μm, thus exhibiting a very high degree of sphero-telecentricity as referenced to the 16 mm target surface.

Referring now to FIG. 22C, embodiments of the 16 mm sphero-telecentric objective (h) of FIG. 22A using aspheric optics will be discussed. As illustrated therein, the objective (h) includes three groups of optics in embodiments illustrated in FIG. 22C. As illustrated therein, a sphero-telecentric objective imaging to a 16 mm radius of curvature over a 6.4 mm field of view is prescribed using a combination of spherical (normal glass) and aspheric optics including elements in three groups. The groups include a first doublet followed by a double-sided asphere and a final doublet, The aspheric surfaces are mild aspheres, requiring less than 5 μm depth to remove from the sphere, a prescription for defining and asphere as is known in the art. The working distance (final lens to cornea) is 30 mm, The maximum diameter of the objective is 33 mm. The system images to an angle accuracy of 0.01 degree, with an optical path length consistent to 0.3 μm, thus exhibiting a very high degree of sphero-telecentricity as referenced to the 16 mm target surface, using fewer lens elements than the spherical optic design of FIG. 22B.

Figure 23B:
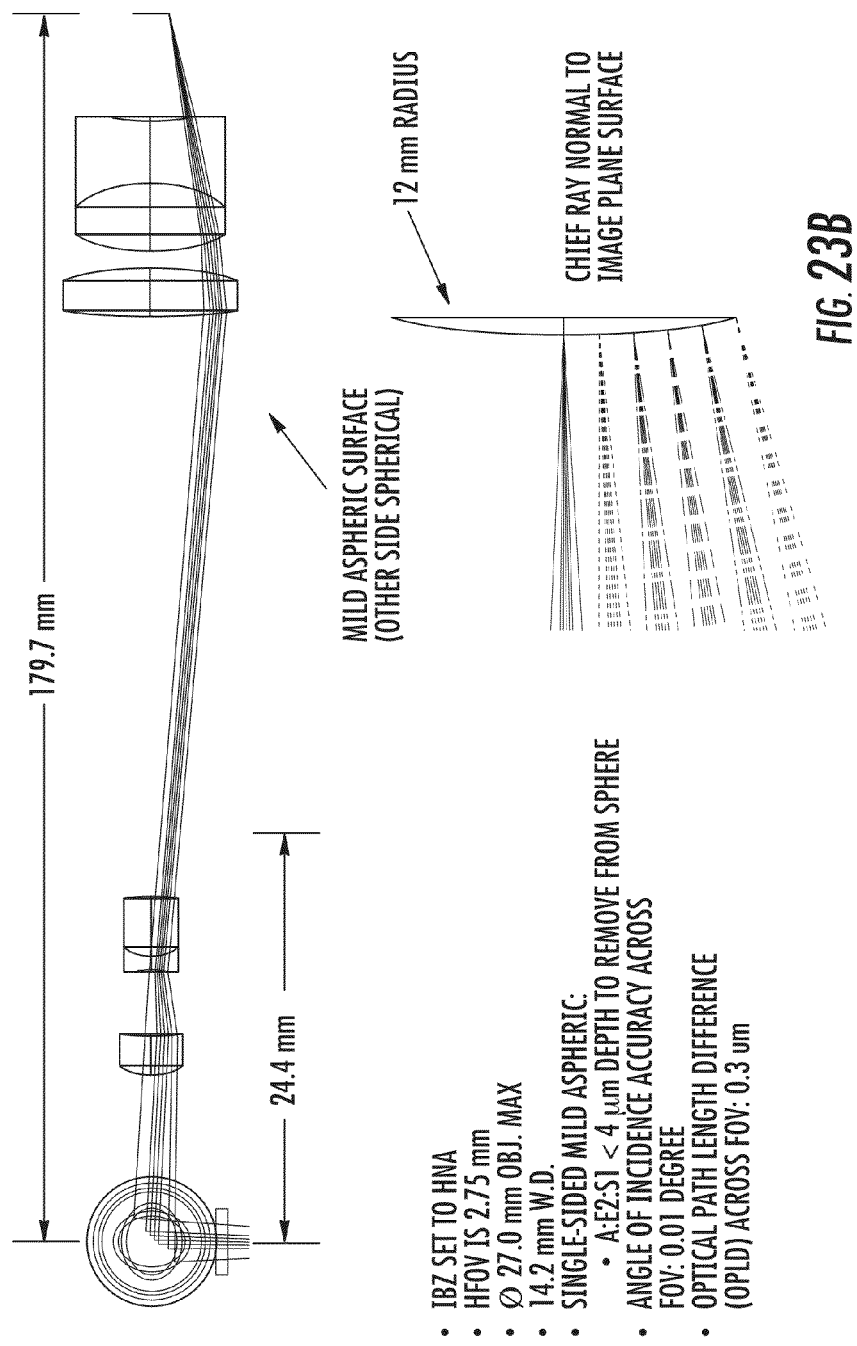

Referring now to FIGS. 23A and 23B, diagrams illustrating a sphero-telecentric system using spherical optics and having a 12 mm radius of curvature in accordance with some embodiments of the present inventive concept. As illustrated in FIG. 23A, the 12 mm sphero-telecentric system using spherical optics includes 6 lens groups. In particular, the sphero-telecentric objective imaging to a 12 mm radius of curvature over a 5.5 mm field of view is prescribed using spherical (normal glass) optics comprising elements in six groups. The groups include a first pair of doublets followed by a third doublet, a fourth doublet, a singlet and a final doublet. The working distance (final lens to cornea) is about 14 mm. The maximum diameter of the objective is about 22.6 mm. The system images to an angle accuracy of 0.01 degree, with an optical path length consistent to 0.3 um.

As illustrated in FIG. 23B, a 12 mm sphero-telecentric system using aspheric optics includes 4 lens groups, reduced from 6 in the embodiment discussed with respect to FIG. 23A. In particular, a sphero-telecentric objective imaging to a 12 mm radius of curvature over a 5.5 mm field of view is prescribed using spherical (normal glass) and aspheric optics includes elements in four groups. The four groups include a first singlet, a first doublet, a first single-sided asphere, and a final doublet. The aspheric surface is a mild asphere, which may require less than 4.0 mm depth to remove from the sphere. The working distance (final lens to cornea) is about 14.2 mm. The maximum diameter of the objective is about 27 mm. The system images to an angle accuracy of 0.01 degree, with an optical path length consistent to 0.3 um.

Figure 24A:
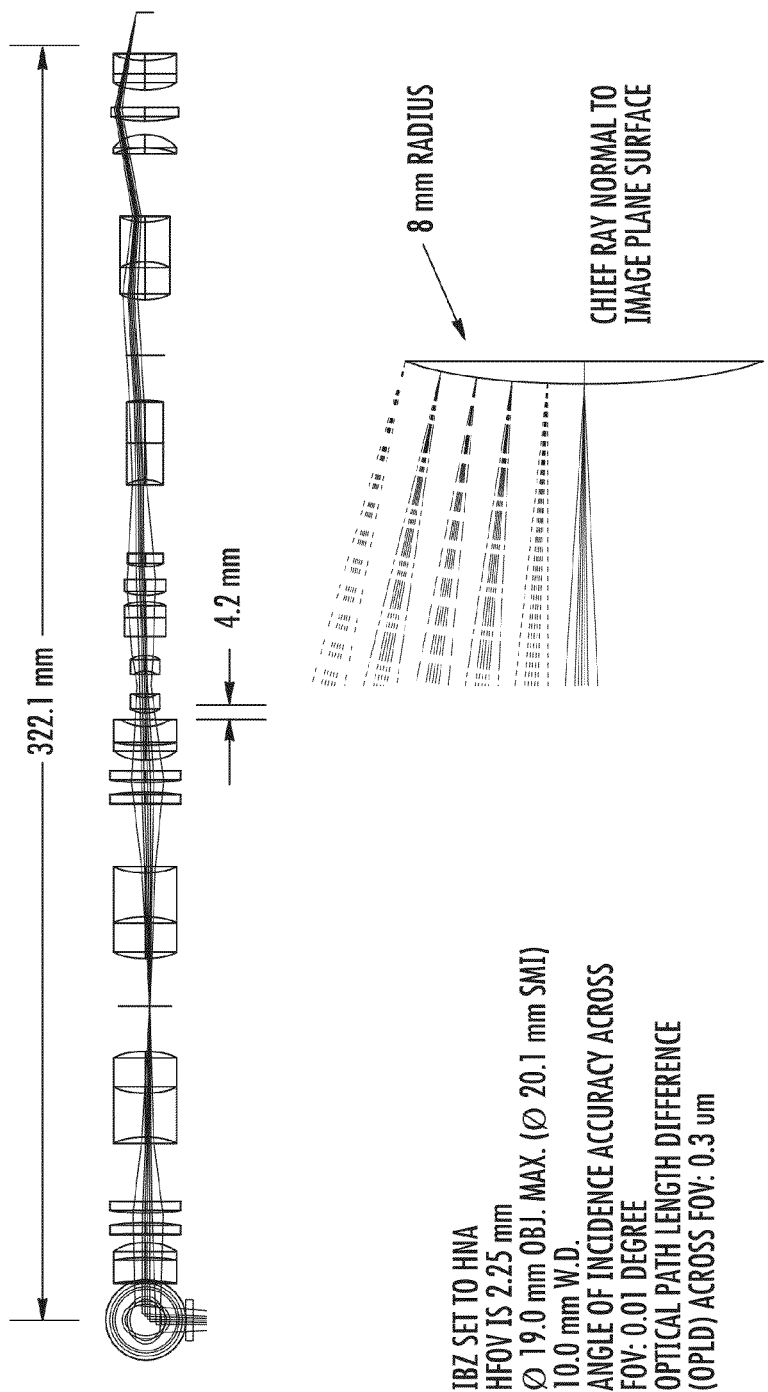
FIGS. 24A and 24B are diagrams illustrating elements of sphero-telecentric systems having an 8 mm radius of curvature in accordance with some embodiments of the present inventive concept.
Figure 24B:
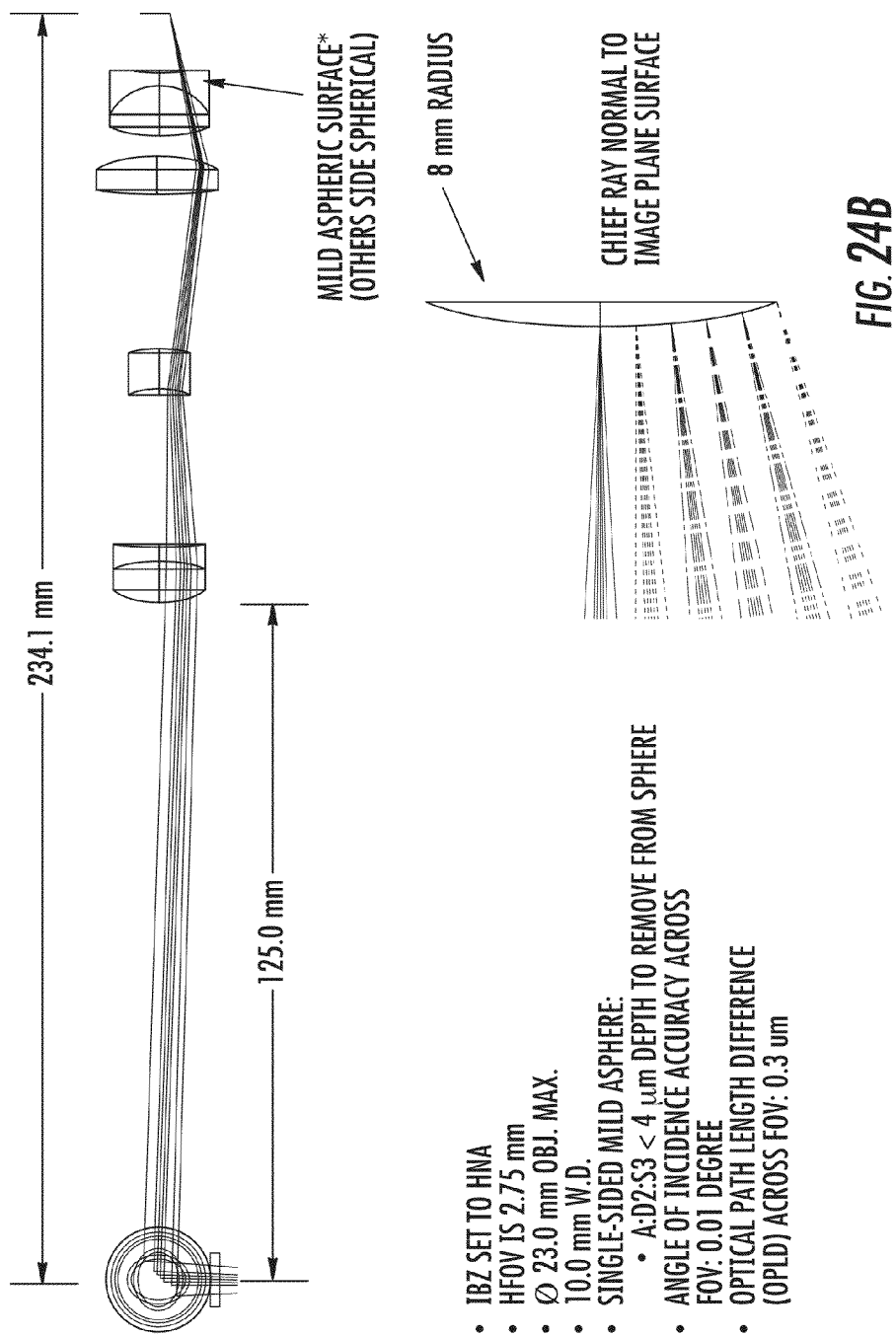

Referring now to FIGS. 24A and 24B, diagrams illustrating a sphero-telecentric system having a 8 mm radius of curvature in accordance with some embodiments of the present inventive concept will be discussed. As illustrated in FIG. 24A, the 8 mm sphero-telecentric system using spherical optics includes a complicated series of optics. In particular, a sphero-telecentric objective imaging to an 8 mm radius of curvature over a 4.5 mm field of view is prescribed using spherical (normal glass) optics including elements in multiple groups as illustrated in FIG. 24A. The working distance (final lens to cornea) is about 10 mm. The maximum diameter of the objective is about 19 mm. The system images to an angle accuracy of 0.01 degree, with an optical path length consistent to 0.3 μm. The complex design illustrated in FIG. 24A is provided to illustrate the variety of designs that may be brought to bear on the problem.

As illustrated in FIG. 24B, the 8 mm sphero-telecentric system using aspheric optics reduces the complicated set of optics illustrated in FIG. 24A to optical elements arranged in 4 groups. In particular, a sphero-telecentric objective imaging to an 8 mm radius of curvature over a 5.5 mm field of view is prescribed using spherical (normal glass) and aspheric optics comprising elements in four groups. The four groups include a first doublet, a first singlet, a first single-sided asphere, and a final doublet. The aspheric surface is a mild asphere, requiring less than about 4 μm depth to remove from the sphere. The working distance (final lens to cornea) is about 10 mm. The maximum diameter of the objective is about 23 mm. The system images to an angle accuracy of 0.01 degree, with an optical path length consistent to 0.2 μm. The degree of path length constancy in this design is better than 0.005% over the 5.5 mm field of view.

Figure 25:
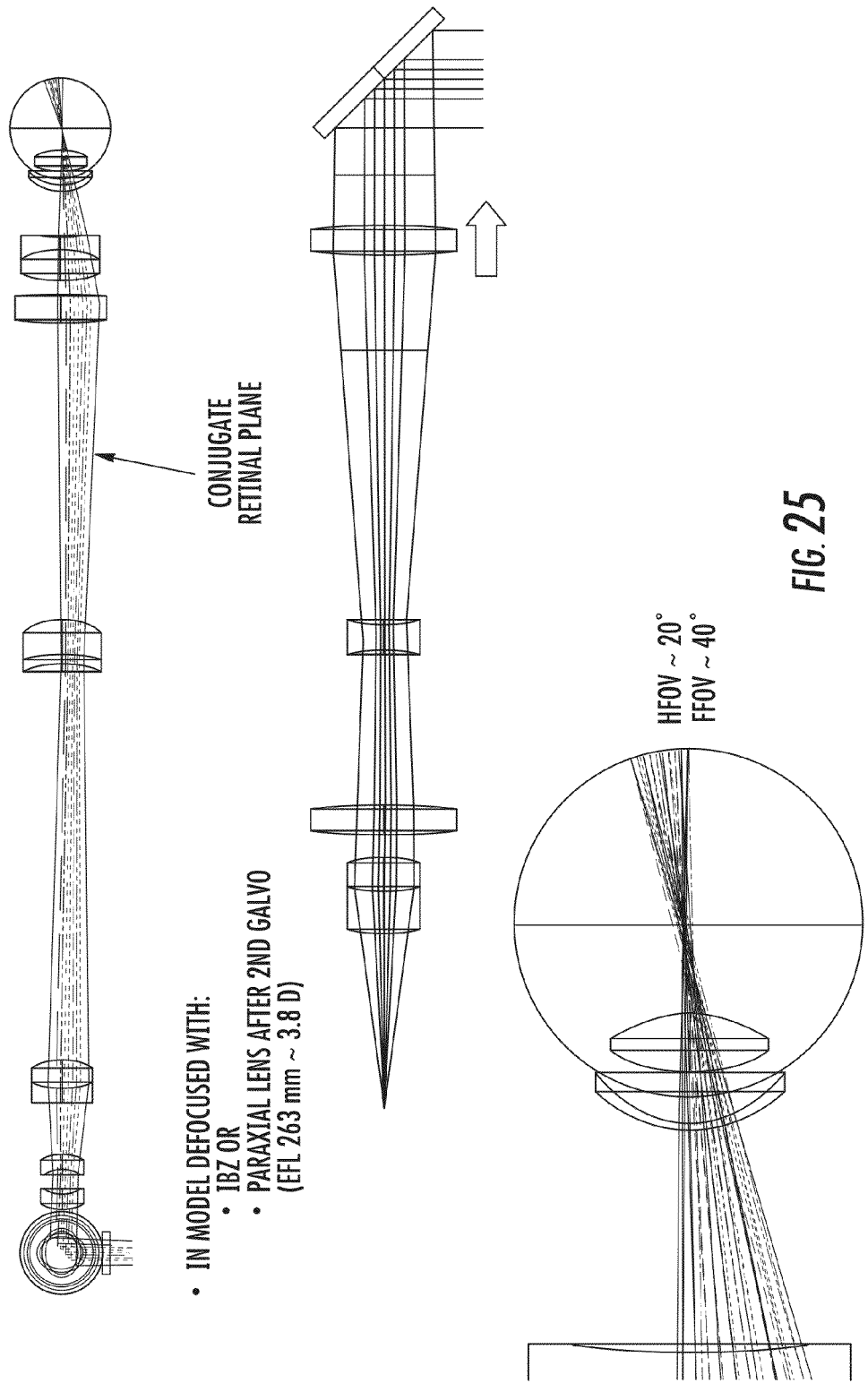
FIG. 25 illustrates a sphero-telecentric system having 12 mm radius of curvature in accordance with some embodiments of the present inventive concept.
Figure 26:
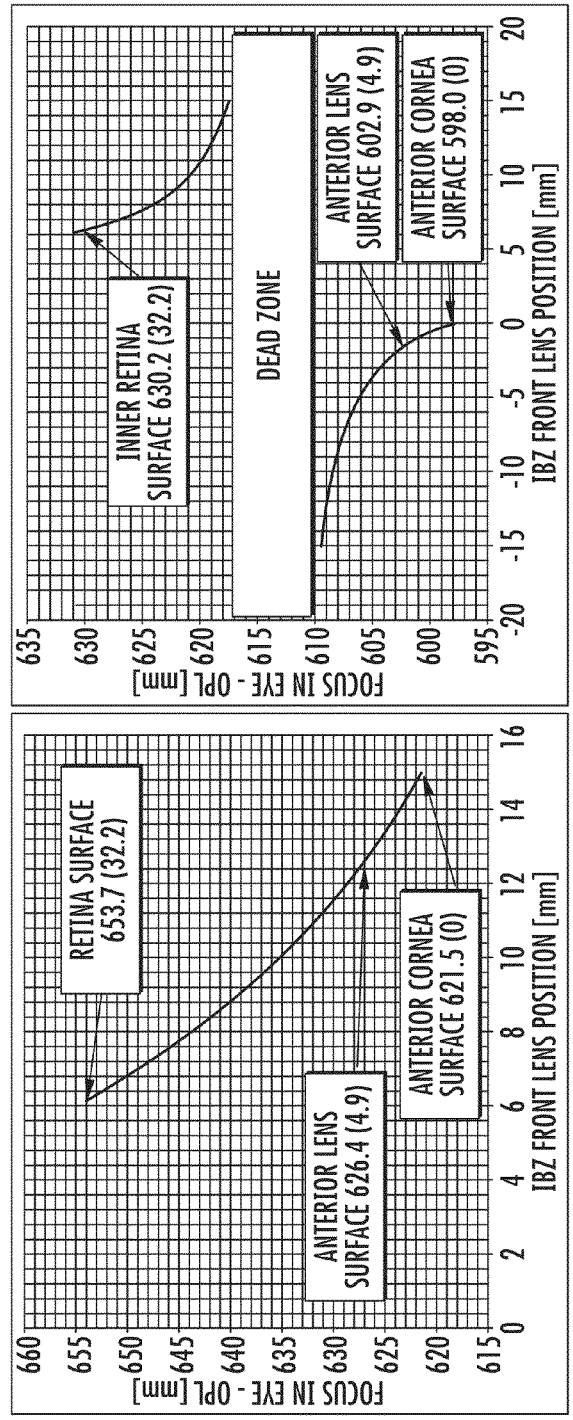
FIG. 26A and 26B are graphs illustrating two modes of imaging using a 12 mm radius of curvature sphero-telecentric system in accordance with some embodiments of the present inventive concept.

Referring now to FIG. 25, a sphero-telecentric system having a 12 mm radius of curvature defocused to image to the retina in accordance with some embodiments of the present inventive concept will be discussed. It will be understood that although embodiments of FIG. 25 are discussed with respect to a 12 mm sphere-telecentric system, embodiments of the present inventive concept are not limited to this configuration. For example, 8 mm and 16 mm sphero-telecentric are examples of other system designs that can be defocused using the same techniques discussed below with respect to FIG. 25 without departing from the scope of the present inventive concept.

Referring now to FIG. 25, a sphero-telecentric system can be defocused using, for example, an IBZ or paraxial lens inserted after the second galvo (EFL 263 mm~3.8 D). A unique characteristic of the sphero-telecentric imaging system combined with the Input Beam Zoom (IBZ) is the ability to shift between imaging the anterior and posterior segments of the eye with a known degree of telecentricity without adding or subtracting lenses from the system.

In embodiments illustrated in FIG. 25, using a sphero-telecentric system having a 12 mm radius of curvature sphero-telecentric objective, the retina is imaged across a 40 degree field of view (FOV) by counter-intuitively shifting Lens (c) of the IBZ forward 6.5 mm relative to the position for cornea imaging. This adds power to the IBZ, and shifts the focus backwards to an intermediate position within the sphero-telecentric objective. With sufficient increase in focusing power, an internal conjugate forms, and this internal conjugate is then imaged forward to the retina. For OCT imaging, the reference arm path length is adjusted to shift the interferometric condition from the front of the eye to the back. In this mode of operation, the transition between an anterior imaging telecentric system to a posterior imaging scan pivoting system is accomplished without the addition or subtraction of any lens element.

As discussed above, embodiments are not limited to using the IBZ. For example, the same or similar effect may be achieved by adding a paraxial lens to the system, for example, after the second galvo. In some embodiments, a 3.8 D lens may be used.

Referring now to FIGS. 26A and 26B, graphs illustrating two modes of imaging using a 12 mm radius of curvature in a sphero-telecentric system in accordance with some embodiments of the present inventive concept will be discussed. The sphero-telecentric design according to some embodiments of the present inventive concept may enable multiple application modes. For example, in a first mode, the IBZ focus control may be used to scan across an entire depth of an eye from cornea through retina with a continuous motion of the IBZ front lens (lens c). In this mode, the front lens of the IBZ is moved forward sufficiently to move a beam conjugate into an interstitial space within the sphero-telecentric objective. This conjugate is then imaged forward of the sphero-telecentric lens to a structure of the eye. As the front lens of the IBZ is positioned increasingly forward, increasing the optical power of the IBZ, the internal, or interstitial, conjugate moves increasingly backwards, and the image of this conjugate is pulled increasingly forward with respect to the subject structure, as illustrated in FIG. 26A. At maximum IBZ power, the conjugate is imaged at the cornea. At minimum IBZ power, the conjugate is imaged at the retina. As illustrated in FIG. 26A, the function is continuous. A coordinated control of the reference arm of the OCT engine with the focus of the IBZ allows acquisition of OCT data continuously along the length of the eye or other translucent object. In this mode, the working distance is increased such that the subject is at a working distance greater than the sphero-telecentric radius of curvature. In 12 mm sphero-telecentric radius embodiments, the working distance for the eye becomes 37.5 mm. Note that this implies that the imaging is beyond the crossing point of the convergent beams; this system thus works primarily on-axis with a limited field of view (FOV) but is quite suitable for axial length assessment.

In a second mode, the mode described for anterior segment imaging, and extension to posterior segment imaging is enabled. In this second mode, the working distance is constant as described for the sphero-telecentric imaging. With the IBZ focus set to collimation, the cornea surface is imaged. As the IBZ zoom power is reduced by pulling the front lens position back, closer to the negative lens of the IBZ, the focusing power of the system is reduced on interior surfaces of the anterior segment, such as the anterior surface of the crystalline lens may be imaged. This defocusing is insufficient to image through to the retina. To image the retina, the IBZ zoom power is increased, contrary to intuition as discussed above. This is because the conjugate is pulled to the interstitial space of the objective, as discussed above, and then imaged back to the retain. Posterior regions may be imaged so long as they are posterior to the crossing of the scanning rays, by appropriate control of the reference arm and IBZ zoom, as illustrated in FIG. 26B.

Figure 27:
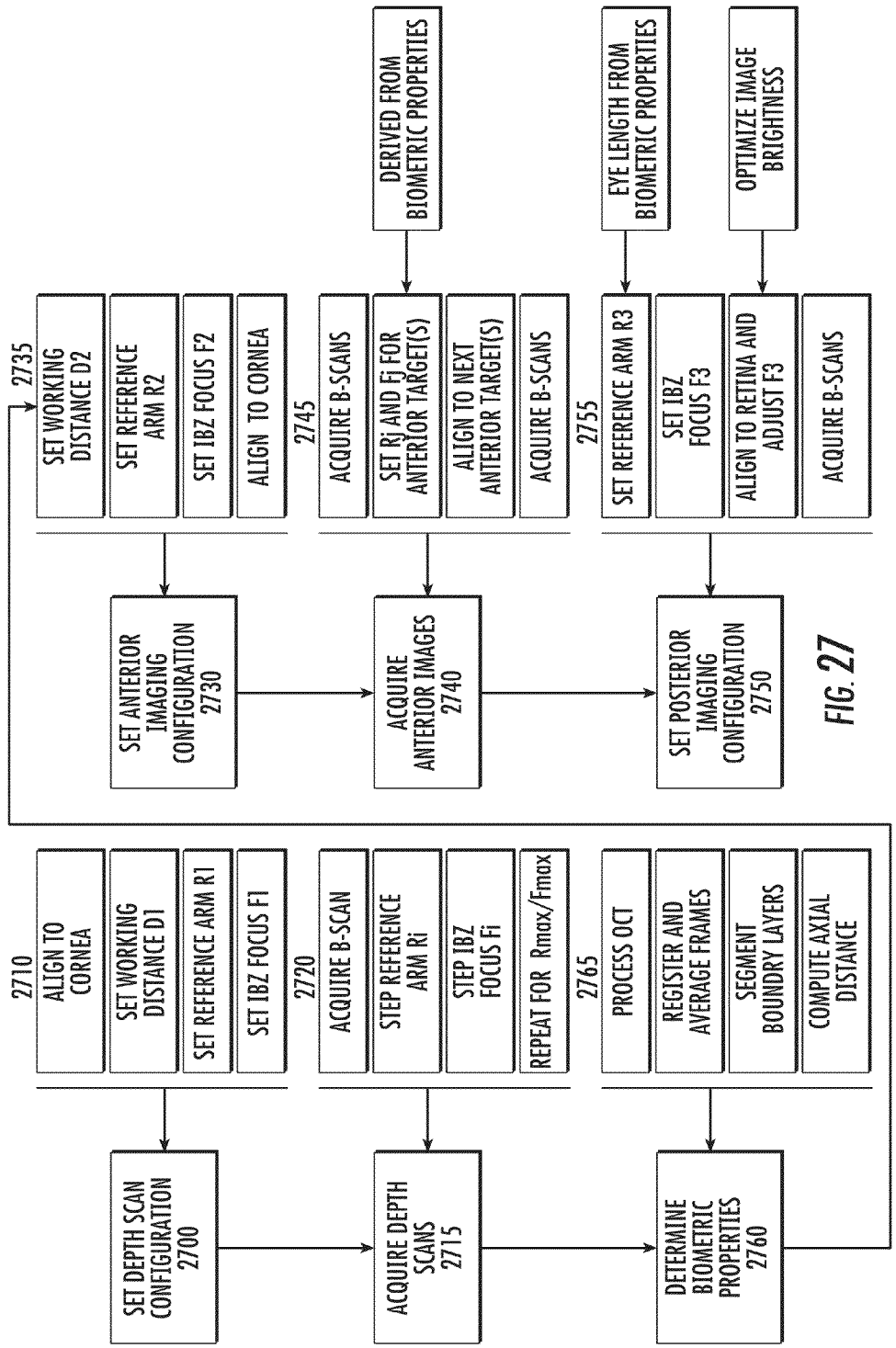
FIG. 27 is a flowchart illustrating operations for an imaging ocular biometer using sphero-telecentric optics in accordance with some embodiments of the present inventive concept.

Referring now to FIG. 27, a flowchart illustrating operations for an imaging ocular biometer using sphero-telecentric optics in accordance with some embodiments of the present inventive concept will be discussed. The dual mode capability of the sphero-telecentric imaging system enables a unique and novel imaging biometer well suited to ocular diagnostics. As illustrated in FIG. 27, axial biometry is measured with the system in depth scan mode (Mode 1 of FIG. 26A), and the measurements derived from the axial biometry are used to image both anterior and posterior structures of the eye in the second, imaging mode.

Operations begin at block 2700 by setting a depth scan configuration. The system is aligned to the cornea; the working distance D1 (here D1 refers to working distance, not to the IBZ lens spacing D1 as used previously) is set to the depth scanning configuration, for example, 37.5 mm; the reference arm is set to the appropriate position for imaging the cornea; and the IBZ focus is set to the collimated position (blocks 2710).

A series of scans are acquired throughout the depth (block 2715). In some embodiments, a limited range B-scan, for example, 2 mm, is acquired at least one time, and if multiple times they may be averaged for improved signal-to-noise; the reference arm path length is increased by a fraction of the eye length; the IBZ focus power is increased according to the relationship as illustrated in FIG. 26B (blocks 2720). Operations of blocks 2720 may be repeated, for example, a second B-scan is acquired; the reference arm step is selected to be a fraction of the individual OCT A-scan length, for example $1/10^{th}$ the distance of the FDOCT scan window, so that subsequent scans may be aligned; and this process is repeated until the entire eye length is mapped (blocks 2715, 2720). In some embodiments, a sequence of about 100 B-scans stepped at 250 μm, each comprising about 100 A-scans acquired at 32,000 A-scans per second will be map the axial length of the eye in approximately $1/3$ of a second. With 3× averaging, the time increases to only about 1 second. At 70,000 A-scans per second, the acquisition time is back below half a second. This timing is also reasonable for stepping the IBZ lens and the reference arm using electromechanical actuators known in the arts.

The data is processed to identify structures in each B-scan that represent the structures in the eye, using layer segmentation algorithms, or using new algorithms designed for the purpose (blocks 2760 and 2765). By using highly overlapping scan windows, any subject motion during the total scan period may be largely accounted for by registering successive frames and comparing structural offsets compared to the reference arm motion.

A linear data set identifying structural boundaries as a function of axial position is derived, and these positions may be used during the imaging phase to set the system parameters for both anterior and posterior imaging.

Figure 28:
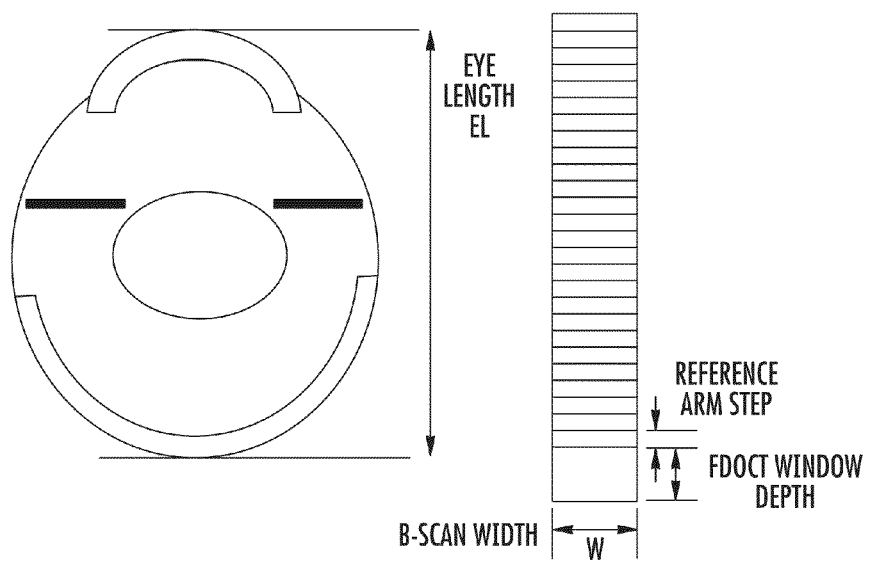
FIG. 28 is a diagram illustrating an axial biometer acquisition in accordance with some embodiments of the present inventive concept.

Referring now to FIG. 28, a diagram illustrating an axial biometer acquisition in accordance with some embodiments of the present inventive concept will be discussed. As illustrated in FIG. 28, the B-scans having a width W are stacked for the entire eye length EL as a function of depth in the eye for the depth scanning mode to be used in ocular biometry.

Figure 29:
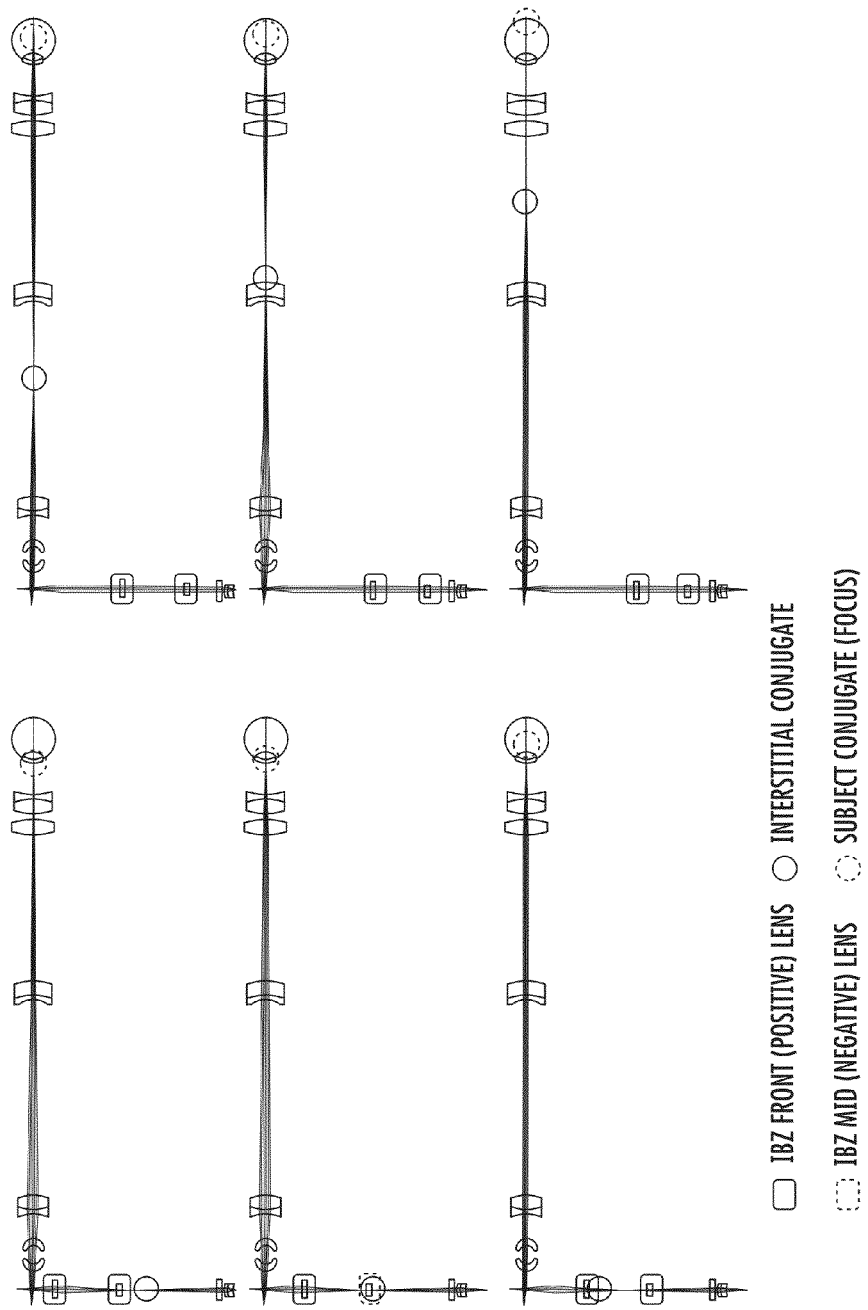
FIG. 29 is a flow diagram illustrating imaging both the anterior and posterior segments of the eye using sphero-telecentric optics in accordance with some embodiments of the present inventive concept.

Referring now to FIG. 29, a flow diagram illustrating imaging both the anterior and posterior segments of the eye in accordance with some embodiments of the present inventive concept will be discussed. Some embodiments of the present inventive concept provide a third mode of operation for sphero-telecentric imaging system with input beam zoom (IBZ). The third mode of operation allows combined axial biometry and anterior and posterior imaging, through continuous exploration of the structures of an eye from cornea through retina using a coordinated change of position of the two movable lenses in the IBZ to shift the focus, together with a shift in the reference arm to coincide the OCT interferometric imaging condition with the focus. In the third mode of operation the working distance is maintained at a fixed imaging distance. In 12 mm imaging radius embodiments, the working distance is about 14 mm. FIG. 29 illustrates a sequence of positions of the IBZ lenses (negative lens b and positive lens c), the resultant interstitial conjugate, and the position of imaging this interstitial conjugate to the subject (the subject conjugate). Thus, the entire length of the eye is imaged as shown by the subject conjugate (dotted circle over various portions of the eye/sample).

Referring now to FIGS. 30A through C, block diagrams of a sphero-telecentric systems and example settings for various modes in accordance with some embodiments of the present inventive concept will be discussed. As illustrated in FIG. 30A, the system includes a fiber input (a); a collimator (b); an input beam zoom (IBZ) (c); a mirror axis 1 (d); a telecentric relay half 1 (e); a telecentric relay half 2 (f); a mirror axis 2 (g); an optical path managed objective (OPMO) (h); and a subject (i). As further illustrated in FIG. 30B, part (c) the input beam zoom (IBZ) is blown up and includes three lenses, a, b and c. Finally, Figure in FIG. 30C, the OPMO or sphero-telecentric objective (STO) includes first through fourth lens groups, I, II, III and IV. The settings for lenses a, b and c of the IBZ (c) and the STO (i) are provided in the various charts of FIGS. 30A-C for modes 1 (imaging mode) and mode 3 (combined imaging/biometry mode) discussed above.

Although settings for mode 2 are not provide, embodiments illustrated in FIGS. 30A-30C are applicable to mode 2 without departing from the scope of the present inventive concept.

Figure 31:
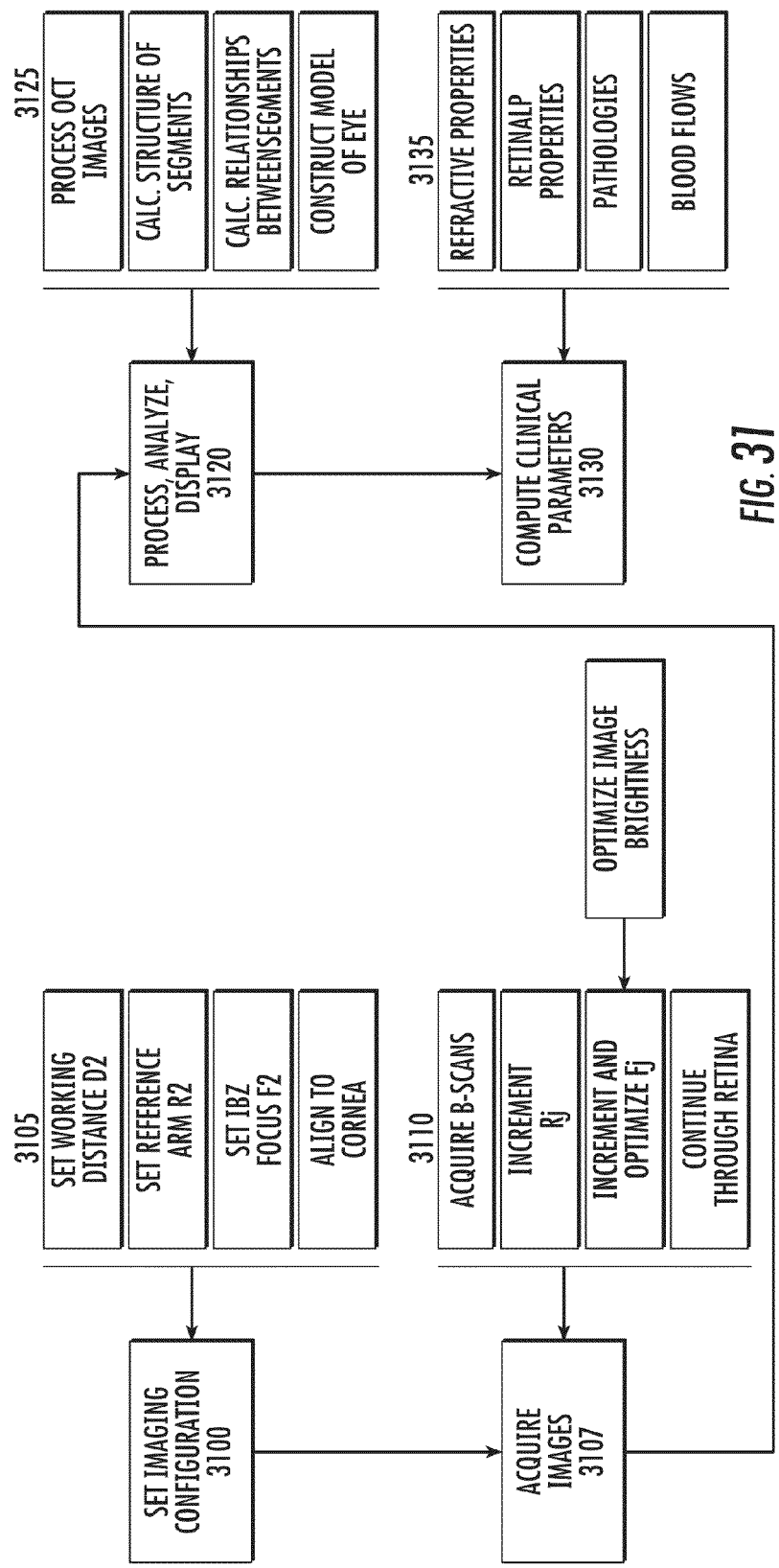
FIG. 31 is a flow chart illustrating operations for imaging ocular biometer using sphero-telecentric optics in accordance with some embodiments of the present inventive concept.

Referring now to FIG. 31, a flow chart illustrating operations for an Imaging Ocular Biometer using sphero-telecentric optics in accordance with some embodiments of the present inventive concept will be discussed. The multi-mode capability of the sphero-telecentric imaging system enables a unique and novel imaging biometer well suited to ocular diagnostics. Operations begin at block 3100 by setting an imaging scan configuration. The system is aligned to the cornea; the working distance D1 is set to the imaging scanning configuration, for example, 14 mm; the reference arm is set to the appropriate position for imaging the cornea; and the IBZ lens positions are set to is set to the cornea imaging positions as prescribed in the table for Mode 3 of FIG. 30 (blocks 3105).

Operations proceed to blocks 3107 and 3110 where a series of scans are acquired throughout the depth. In embodiments illustrated in FIG. 31, B-scans are acquired over the field of view applicable to the imaging position, per the Table. Scans may be acquired one time, or multiple times for averaging; the reference arm path length is increased by a fraction of the eye length; and the IBZ lens settings are modified according to the Table. Until the entire eye is mapped.

The data is then processed to identify structures in each B-scan that represent the structures in the eye, using layer segmentation algorithms, or using new algorithms designed for the purpose (blocks 3120 and 3125). By using highly overlapping scan windows, any subject motion during the total scan period may be largely accounted for by registering successive frames and comparing structural offsets compared to the reference arm motion.

A linear data set identifying structural boundaries as a function of axial position are derived, and these positions may be used is establish biometric properties of the eye, including an axial eye length, and lengths to or thicknesses of major structures of the eye including cornea thickness, anterior segment depth, crystalline lens thickness, posterior chamber depth, retinal thickness, etc. (blocks 3130 and 3135). Additionally, pathologies may be identified as a function of position within the eye, measured, and unambiguously referenced to structures of the eye. Oct angiographic techniques, including Doppler OCT and other methods of extracting vascular information known in the art may be applied to discern blood flow properties of the uveal and retinal circulatory systems of the eye.

Thus, as briefly discussed above, some embodiments of the present inventive concept provide a system design that can serve a unified purpose of imaging the ultrastructure of the inner eyelid, the meibomian ducts, the tearfilm meniscus and the cornea with a single compact handpiece. In some embodiments, the system may used to image a spherical surface onto a plane with less than 100 µm deviation, with a resolution of better than 20 µm, across a 15 mm field of view. A flatness of better than 10 µm may be provided. The system may provide high quality, easily interpreted images of the inner eyelid, tear film, cornea and angle, which allow diagnostic assessment of structures relevant to dry eye disease and cornea dystrophies.

Some embodiments of the present inventive concept provide a system design that can serve to improve the imaging of curved surfaces such as the cornea by increasing the degree of telecentricity to the curved surface, balanced to avoid excessive specular reflections arising from perfect telecentricity to reflective surfaces.

Some embodiments of the present inventive concept provide a system design that can serve a unified purpose of combining ocular biometry with imaging of the anterior and posterior segments of the eye though one of multiple modes of measurement in the same optical system, without requiring the insertion or removal of a lens from the system to switch between imaging modes.

Some embodiments of the present inventive concept provide for an input beam shaping mechanism that enables numerical aperture and focal control that may be extended to a range of optical beam imaging systems.

Example embodiments are described above with reference to block diagrams and/or flowchart illustrations of systems and devices. The functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A scanning optical beam imaging system for imaging a surface with convex curvature, the system comprising:
  a source of optical radiation coupled to an optical fiber, wherein the optical fiber is coupled to an input of the scanning optical beam imaging system;
  an input lens assembly configured to direct a beam of optical radiation from the optical fiber to a beam scanning assembly of the imaging system;
  a lens assembly following the beam scanning assembly configured to transform the scanned beam of optical radiation into a set of non-parallel beams diverging from an optical axis of the lens assembly;
  an objective lens assembly configured to transform the diverging set of non-parallel beams to a set of non-parallel rays converging in object space, wherein the converging rays focus along a curved focal surface in object space between the objective lens assembly and a region of intersection of the rays;

wherein a radius of curvature of a focal surface is greater than zero and less than an axial distance between a distal objective lens surface and the focal surface; and wherein the rays in object space are substantially perpendicular to the focal surface; and wherein optical path lengths of the set of rays measured from the optical fiber input to the focal surface are substantially equal.

2. The system of claim 1, wherein the objective lens assembly comprises lens elements arranged in four or fewer lens groups.

3. The system of claim 2, wherein the objective lens assembly comprises an aspheric optical element.

4. The system of claim 1, wherein the scanning optical beam imaging system is in a sample arm of an optical coherence tomography imaging system.

5. The system of claim 1, wherein the input lens assembly comprises a set of at least three lens groups arranged along the optical axis between the optical fiber and the beam scanning assembly, wherein the input lens assembly further comprises:
   at least one positive lens group;
   at least one negative lens group;
   means for adjusting positions of two of the lens groups along the optical axis between the optical fiber and the beam scanning assembly, wherein adjusting positions of two of the lens groups is performed one of in unison or separately; and
   wherein positions of the lens groups along the optical axis map to an effective numerical aperture and an effective focal length of the imaging system.

6. An optical coherence tomography imaging system for imaging a curved surface, the system comprising:
   a source of optical radiation coupled to an optical fiber, wherein the optical fiber is coupled in a sample arm of the optical coherence tomography imaging system to an input of the scanning optical beam imaging system;
   an input lens assembly that directs a beam of optical radiation from the optical fiber to a beam scanning assembly;
   a lens assembly following the beam scanning assembly configured to transform the scanned beam of optical radiation to a set of non-parallel beams diverging from an optical axis of the lens assembly;
   an objective lens assembly configured to transform the diverging set of beams to a set of non-parallel rays converging in object space,
   wherein the converging beams focus along a curved focal surface in object space between the objective lens assembly and a region of intersection of the rays;
   wherein a radius of curvature of the focal surface is greater than zero and less than an axial distance between a distal objective lens surface and the focal surface;
   wherein the rays in object space are substantially perpendicular to the focal surface; and
   wherein optical path lengths of the set of rays measured from the optical fiber to the focal surface are substantially equal.

7. The system of claim 6, wherein the objective lens assembly comprises lens elements arranged in four or fewer lens groups.

8. The system of claim 7, wherein the objective lens assembly comprises an aspheric optical element.

9. The system of claim 6, wherein the input lens assembly comprises a set of at least three lens groups arranged along the optical axis between the optical fiber and the beam scanning assembly, wherein the input lens assembly further comprises:
   at least one positive lens group;
   at least one negative lens group;
   means for adjusting positions of two of the lens groups along the optical axis between the optical fiber and the beam scanning assembly, wherein adjusting positions of two of the lens groups is performed one of in unison or separately; and
   wherein positions of the lens groups along the optical axis map to an effective numerical aperture and an effective focal length of the imaging system.

* * * * *

UNITED STATES PATENT AND TRADEMARK OFFICE
CERTIFICATE OF CORRECTION

PATENT NO. : 8,864,309 B2
APPLICATION NO. : 13/705867
DATED : October 21, 2014
INVENTOR(S) : Buckland et al.

It is certified that error appears in the above-identified patent and that said Letters Patent is hereby corrected as shown below:

In the Specification:
Column 12, Line 31: Please correct "cornea interface,"
to read -- cornea interface. --

Signed and Sealed this
Twenty-fourth Day of February, 2015

Michelle K. Lee
*Deputy Director of the United States Patent and Trademark Office*